United States Patent [19]
Gritz et al.

[11] Patent Number: 5,691,170
[45] Date of Patent: Nov. 25, 1997

[54] GENERATION OF HYBRID GENES AND PROTEINS BY VIRUS-MEDIATED RECOMBINATION

[75] Inventors: Linda R. Gritz, Somerville; Dennis L. Panicali, Acton, both of Mass.

[73] Assignee: Therion Biologics, Cambridge, Mass.

[21] Appl. No.: 412,609

[22] Filed: Mar. 29, 1995

Related U.S. Application Data

[63] Continuation of Ser. No. 929,698, Aug. 12, 1992, abandoned, which is a continuation of Ser. No. 526,248, May 18, 1990, abandoned, which is a continuation-in-part of Ser. No. 510,125, Apr. 17, 1990, abandoned, which is a continuation-in-part of Ser. No. 340,052, Apr. 18, 1989, abandoned.

[51] Int. Cl.$^6$ .................................................. C12N 15/62
[52] U.S. Cl. .................... 435/69.7; 435/177.3; 536/23.4
[58] Field of Search .............................. 435/69.7, 172.3; 536/23.4

[56] References Cited

U.S. PATENT DOCUMENTS

| | | | |
|---|---|---|---|
| 4,336,336 | 6/1982 | Silhavy et al. | 435/172.3 |
| 4,593,002 | 6/1986 | Dulbecco | 435/172.3 |
| 4,603,112 | 7/1986 | Paoletti et al. | 435/235.1 |
| 4,769,330 | 9/1988 | Paoletti et al. | 435/172.3 |
| 5,017,487 | 5/1991 | Stunnenberg et al. | 435/172.3 |
| 5,021,347 | 6/1991 | Yasui et al. | 435/235 |

FOREIGN PATENT DOCUMENTS 8706262  10/1987  WIPO ..................... C12N 15/00

OTHER PUBLICATIONS

Weber, et al., *Nucleic Acids Research*, 11(16):5661–5669 (1983).
Gray, et al. *Journal of Bacteriology*, 166(2):635–643 (1986).
J. Ball, et al., *J. Virol.* 61:1788–1795 (1987).
Spyropuolos, et al., *J. Virol.*, 62:1046–1054 (1988).
King, et al., *Cell*, 29:921–928 (1982).
Tolskaya, et al., *Virology*, 124:121–132 (1983).
Fields, et al., *Cell*, 28:303–313 (1982).
Morin, et al., *Proc. Natl. Acad. Sci. USA*, 84:4626–4630 (1987).
Lowe, et al., *Proc. Natl. Acad. Sci. USA*, 84:3896–3900 (1987).
Panicali, et al., *Proc. Natl. Acad. Sci. USA* 79:4927–4931 (1982).
Paoletti, et al., *Proc. Natl. Acad. Sci. USA* 81:193–197 (1984).
Kieny, et al., *Nature*, 312:163–166 (1984).
Yilma et al., *Science*, 242:1058–1061 (1988).
Starcich, et al., *Cell*, 45:637–648 (1986).
Hahn, et al., *Science*, 232:1548–1553 (1986).
Mathews, et al., *Proc. Natl. Acad. Sci. USA*, 83:9709–9713 (1986).
Nara, et al., *J. Virol.*, 62:2622–2628 (1988).
Streuli, et al., *Proc. Natl. Acad. Sci. USA*, 78:2848–2852 (1981).
Weck, et al., *Nucleic Acids. Res.*, 9:6153–6166 (1981).
Keil, et al., *Virology*, 170:392–407 (1989).
Smith et al., *Science* 228: 1315–1317, 14 Jun. 1985.
Nogami et al., *J. of Bact.* 164(2):797–801, Nov. 1985.
Yamada et al., *J. Biochem* 102(3):455–464, Mar. 1987.
Sire et al., *J. Immunol.* 140(7):2422–2430, 01 Apr. 1988.
Bollag et al. (1989) Ann. Rev. Genet. 23 :199–225.
Starcik et al. (1986) Cell, vol. 45, pp. 637–648.

*Primary Examiner*—John Ulm
*Attorney, Agent, or Firm*—Sewall P. Bronstein; Ronald L Eisenstein; David S. Resnick

[57] ABSTRACT

The ability of viruses to undergo recombination within tandemly arranged homologous sequences can be utilized to generate chimeric genes and proteins. Tandemly arranged homologous sequences will rapidly degenerate in a random fashion to yield a single copy comprised of portions of both original sequences. Therefore, a recombinant virus which contains two related but non-identical genes in tandem array yields a population of recombinant viruses which contain a spectrum of hybrid sequences derived from recombination between the original genes. The viruses, therefore, contain hybrid DNA sequences that encode proteins with new epitopes or different combinations of epitopes. Vaccines are derived which may afford protection against a broad spectrum of antigen types.

9 Claims, 18 Drawing Sheets

GENERATION OF HYBRID GENES AND PROTEINS BY VIRUS-MEDIATED RECOMBINATION

RELATED APPLICATIONS

This application is a continuation of application Ser. No. 07/929,698, filed 12 August of 1992, now abandoned, which is a continuation of application Ser. No. 07/526,248, filed 18 May of 1990, now abandoned, which is a continuation-in-part of application Ser. No. 07/510,125, filed 17 April of 1990, now abandoned, which is a continuation-in-part of application Ser. No. 07/340,052, filed 18 April of 1989, now abandoned.

GOVERNMENT SUPPORT

The work leading to this invention was supported by one or more research grants from the U.S. Government.

BACKGROUND

Recombination involves the breakage and cross-wise reunion of nucleic acid strands within homologous sequences. This phenomenon is a critical feature of evolution, particularly in eukaryotes; genetic exchange through recombination works constantly to blend and rearrange genomic sequences, creating genetic diversity by producing different combinations of genetic alleles.

Intermolecular recombination is the term used to describe recombination between two different nucleic acid molecules, for example, between two homologous chromosomes during meiosis, or between different viral genomes present in the same infected cell. Intermolecular recombination has been documented in a number of different animal viruses, including RNA viruses such as picornaviruses (King et al., 1982. Cell 29:921–928; Tolskaya et al., 1983. Virology 124:121–132) and influenza virus (Fields and Winter. 1982. Cell 28:303–313) as well as DNA viruses.

The phenomenon of intermolecular recombination between viral genomes and exogenous DNA has been exploited for the development of certain viruses, including adenoviruses (Morin et al. 1987. Proc. Natl. Acad. Sci. USA 84:4626–4630), herpesviruses (Lowe et al. 1987. Proc. Natl. Acad. Sci. USA 84:3896–3900) and poxviruses (Panicali and Paoletti. 1982. Proc. Natl. Acad. Sci. USA 79:4927–4931; Paoletti and Panicali, U.S. Pat. No. 4,603,112) as live vectors for the cloning and expression of foreign DNA sequences. Vaccinia virus, an orthopox virus, has been most extensively characterized and developed as an infectious eukaryotic cloning vector (Paoletti and Panicali, U.S. Pat. No. 4,603,112). Heterologous genes, including those encoding antigens from a variety of pathogens, have been expressed in this vector system. In all cases, the foreign gene product expressed by the recombinant vaccinia virus was similar or identical to the gene product synthesized under native conditions. In some instances, vaccination of laboratory animals with recombinant vaccinia viruses has protected these animals against challenge with the correlate pathogens (Paoletti et al. 1984. Proc. Natl. Acad. Sci. USA 81:193–197; Kieny et al. 1984. Nature 312:163–166; Alizon et al. 1984. Nature 312:757–760; Boyle et al. 1985. Gene 35:169–177; Vilma et al. 1988. Science 242:1058–1061).

In addition to intermolecular recombination (recombination between different nucleic acid molecules), intramolecular recombination (recombination between homologus sequences present on a single nucleic acid molecule) also has been documented in a number of animal viruses, including picornaviruses, influenza virus, herpesviruses, and poxviruses. In vaccinia virus, for example, it has been shown that tandemly duplicated identical sequences are genetically unstable (Panicali and Paoletti. 1982. Proc. Natl. Acad. Sci. USA, 79:4927–4931; Ball. 1987. J. Virol. 61:1788–1795; Spyropoulos et al. 1988. J. Virol. 62:1046–1054); intramolecular recombination between these identical sequences results in a condensation of the duplicated structure to yield a single copy of the previously duplicated sequences. Recombinant vaccinia viruses that contain such tandem duplications can be stably maintained only when a gene encoding a selectable marker (such as the thymidine kinase gene, or a gene encoding drug resistance) is placed between the duplicated sequences. The intramolecular recombination event that results in condensation of the duplicated structure also results in excision of the marker gene. Thus, selection for the function of the marker gene also selects for the presence of the duplication.

Although intramolecular recombination between tandemly arranged, identical DNA sequences has been documented, there has thus far been no examination of in vivo intramolecular recombination, between non-identical, but related (i.e., partially homologous) DNA sequences.

Different but related genes have been documented in a variety of natural systems. One example may be found among certain pathogens that exhibit antigenic variation. For example, the occurrance of antigenic and genomic variation in human immuno-deficiency virus (HIV), the causative agent of AIDS, has been demonstrated by a number of researchers (Starcich et al. 1986. Cell, 45:637–648; Hahn et al. 1986. Science, 232:1548–1553). These studies have revealed that changes are found primarily in the viral envelope (env) gene, which encodes the antigens against which a major component of the antibody response is directed.

The antigenic diversity exhibited by HIV and by other pathogenic organisms presents obstacles to the formulation of vaccines effective against these pathogens, as a vaccine effective against one variant or subtype may fail to protect against related strains. In order to develop successful vaccination protocols for these pathogens it will be necessary to elicit immune responses capable of recognizing the many variant epitopes present in the family of diverse but related proteins expressed by the pathogens. In order to achieve this, it may be necessary to immunize with a vaccine formulation in which many, if not all, of these variant epitopes are represented.

Another example of different but related genes may be found among the interferons. The interferons (IFN) comprise a group of related proteins that are encoded by three distinct gene families, designated IFN-alpha, IFN-beta, and IFN-gamma. The 14 genes in the IFN-alpha family share approximately 80–90% homology. There is also limited homology (approximately 30%) between genes in the IFN-alpha and IFN-beta families (Joklik, W. K. 1985. Interferons. Pages 281–308 in Fields et al., eds. Virology. Raven Press, N.Y.,N.Y.)

All interferons possess both antiviral and anticellular activity; all cause interference with multiplication of viruses and regulate a variety of cellular functions. However, they vary greatly in the relative extent to which they express these activities in various types of cells. Recently, recombinant DNA technologies have been used in an effort to produce hybrid interferons with altered biological and pharmacological properties. Several hybrid human IFN-alpha interferon species have been constructed (Streuli et al. 1981. Proc.

*Natl. Acad. Sci. USA.* 78:2848–2852; Weck et al. 1981. *Nucleic Acids Res.* 9:6153–6166); these were found to differ greatly in their ability to inhibit the multiplication of various viruses in different mammalian cells and in infected animals (Weck et al. 1982. *Infect. Immun.* 35:660–665). Thus, it may be possible to improve upon the function of natural interferons by generating hybrid interferons with particular applications for clinical use in specific situations, both in the antiviral area and the anticancer area.

SUMMARY OF THE INVENTION

This invention pertains to methods of generating, in vivo, hybrid DNA structures from two related, but different, DNA sequences through a process of genetic recombination within or between viral genomes, and to the expression of the hybrid genes created by these methods in recombinant viruses. Methods of this invention exploit the phenomenon of intramolecular recombination (i.e., recombination between homologous DNA sequences present within a given vital genome). The method is based upon the phenomenon of virus-mediated recombination to generate, in a vital genome, hybrid genes from two related but nonidentical genes, provided that these genes share regions of homology. An example of related genes are genes encoding different variants of a given polypeptide.

According to the methods of this invention, two related genes are introduced in tandem into a viral genome, preferably a poxviral genome. These tandem structures are genetically unstable in viruses. During replication of the vital genome, intramolecular recombination between homologous regions shared by the related genes results in condensation of the duplicated structure to yield a single, hybrid sequence containing portions of the two original sequences. Nevertheless, it is possible to select for viruses that maintain a tandem duplication in the genome if 1) a gene that encodes a selectable marker, under the control of a poxviral transcriptional promoter, is placed between the duplicated sequences and 2) the recombinant poxvirus is propagated under conditions that select for the function of the marker gene. Because recombination between the tandemly arranged genes results in the excision of the marker gene, only those viruses that retain the duplication, together with the intervening marker gene, will survive under selective growth conditions.

A recombinant virus that contains in its genome two tandemly arranged, related genes (separated by an appropriate marker gene) can serve as the progenitor of a population of progeny viruses, each of which contains a different hybrid gene composed of portions of the two original genes. When the parental virus containing tandem DNA sequences separated by a marker gene is allowed to replicate under non-selective growth conditions, progeny viruses generated by intramolecular recombination between homologous sequences will be propagated. This intramolecular recombination event results in excision of the marker gene. Because the recombination event can occur between any homologous regions shared by the two genes, each of the progeny viruses will contain a different hybrid gene resulting from the condensation of the original DNA sequences. Thus, a spectrum of hybrid genes can be generated from two related genes that contain regions of DNA sequence homology. The inclusion of appropriate transcriptional signals upstream of the first of the two duplicated DNA sequences will ultimately allow for the expression of the hybrid genes created by the intramolecular recombination events.

The methods of this invention can be used to produce a mixture of live recombinant viral vectors capable of expressing hybrid genes derived from genes encoding antigenically distinct variants of a given polypeptide. If this polypeptide represents an immunologically important antigen of a pathogenic organism, particularly an organism that exhibits antigenic and genomic variation, the viral vectors so produced may be used as live recombinant vaccines; these vaccines may elicit immune responses to a broad range of serological types and subtypes of the pathogen, as the hybrid genes produced by this method may mimic the genetic changes that occur in the pathogen in nature. In one embodiment of this invention, a recombinant vaccinia virus is constructed to contain in tandem, envelope genes from two different strains of human immunodeficiency virus (HIV), namely the RF and the BH10 strains of HIV-1. The progeny vaccinia viruses generated after intramolecular recombination between the two HIV envelope genes contain a spectrum of hybrid envelope genes derived from the original two genes of the different HIV-1 strains.

This invention can also be used to generate chimeric proteins for other applications. For example, recombination between genes encoding related interferons will generate hybrid genes encoding chimeric proteins with novel pharmacological properties. These chimeric interferons may exhibit improved function by comparison to natural interferons with regard to their applicability for therapeutic use in specific situations.

In addition, vaccinia-mediated recombination between genes encoding related antigens can be used to map type-specific antigenic determinants. For example, a large number of vaccinia recombinants expressing novel hybrid antigens can be generated by recombination between genes encoding related antigens from two different serotypes of an organism. The ability of type-specific monoclonal antibodies to bind individual hybrid proteins in the vaccinia recombinants can be used to map specific epitopes.

BRIEF DESCRIPTION OF THE DRAWINGS

FIG. 1 illustrates a method of generating tandem DNA sequences and chimeric genes in vaccinia using a single-step approach.

FIG. 2 illustrates a step-wise method of generating tandem DNA sequences and chimeric genes in vaccinia.

FIGS. 3A and 3B illustrate construction of a plasmid pABT4075 containing the HIV-1 strain BH10 env gene fused to the *E. coli* lacZ gene. The gene is under the transcriptional control of the vaccinia 7.5K promotor. FIG. 3A shows the intermediate step in creation of pAbT4075 which is constructed of pAbT167. FIG. 3B shows construction of the vector pAbT4075.

FIGS. 4A to 4C illustrates construction of a plasmid (pAbT8523) containing the HIV-1 strain RF env gene. FIG. 4A shows construction of the plasmid pAbT4524B containing both DraI and NotI sites. FIG. 4B shows construction of the plasmid pAbT4533, created by ligating together fragments of the plasmids pAbT4027 and pAbT4524B. FIG. 4C shows construction of pAbT8523, created by ligating sections of two plasmids, pAbT4533 and pRF3HS.

FIGS. 5A and 5B illustrate construction of plasmid pAbT4082 containing the HIV-1 RF env gene modified at the 5' end of the gp41-encoding region. FIG. 5A shows creation of the plasmid pAbT8526, created by ligating fragments of pAbT4533, pAbT8523 and pRF3HS. FIG. 5B shows the creation of pAbT4082, derived from the partial digestion of the plasmid pAbT8526.

FIGS. 6A and 6B illustrate construction of a donor plasmid (pAbT4085) containing the vaccinia virus thymidine kinase gene flanked by two HIV-1 env genes. FIG. 6A shows creation of the plasmid pAbT4083 derived from ligation of fragments from pAbT4075 and pAbT4082. FIG. 6B shows creation of pAbT4085, derived from ligating segments of pAbT4083 and pAbT400. The donor plasmid also contains the RF env gene encoding gp120 under the control of a vaccinia viral promotor and thin lacZ gene fused in-frame to the BH10 env gene.

FIG. 7 is a schematic representation of the steps involved in generating a vaccinia virus containing related, but non-identical genes and steps involved in producing a recombinant virus which has undergone a condensation event to generate a fused HIV-1 env gene.

FIGS. 8A and 8B illustrate construction of plasmid pAbT4105 containing one particular condensed env gene derived from HIV-1 strains BH10 and RF. FIG. 8A shows creation of pAbT4105 derived from ligation of plasmid pAbT2009 to a 3 Kb vaccinia virus genomic fragment containing a condensed env gene. FIG. 8B is a restriction map of plasmid pAbT4105 including sites which define the RF/BH10 Junction.

FIGS. 9A and 9B illustrate the construction and sequencing of a phage (pAbT4106) containing the junction between the HIV-1 RF and BH10 env sequences in the hybrid gene from vAbT168-1. FIG. 9A shows creation of pAbT4106 by ligation of a fragment from plasmid pAbT4105 with phage m13mp19. FIG. 9B shows the partial nucleotide sequences of a portion of pAbT4106 containing the fused env gene, as well as regions of the parental RF and BH10 env genes from pAbT4085.

DETAILED DESCRIPTION OF THE INVENTION

Figure 1:
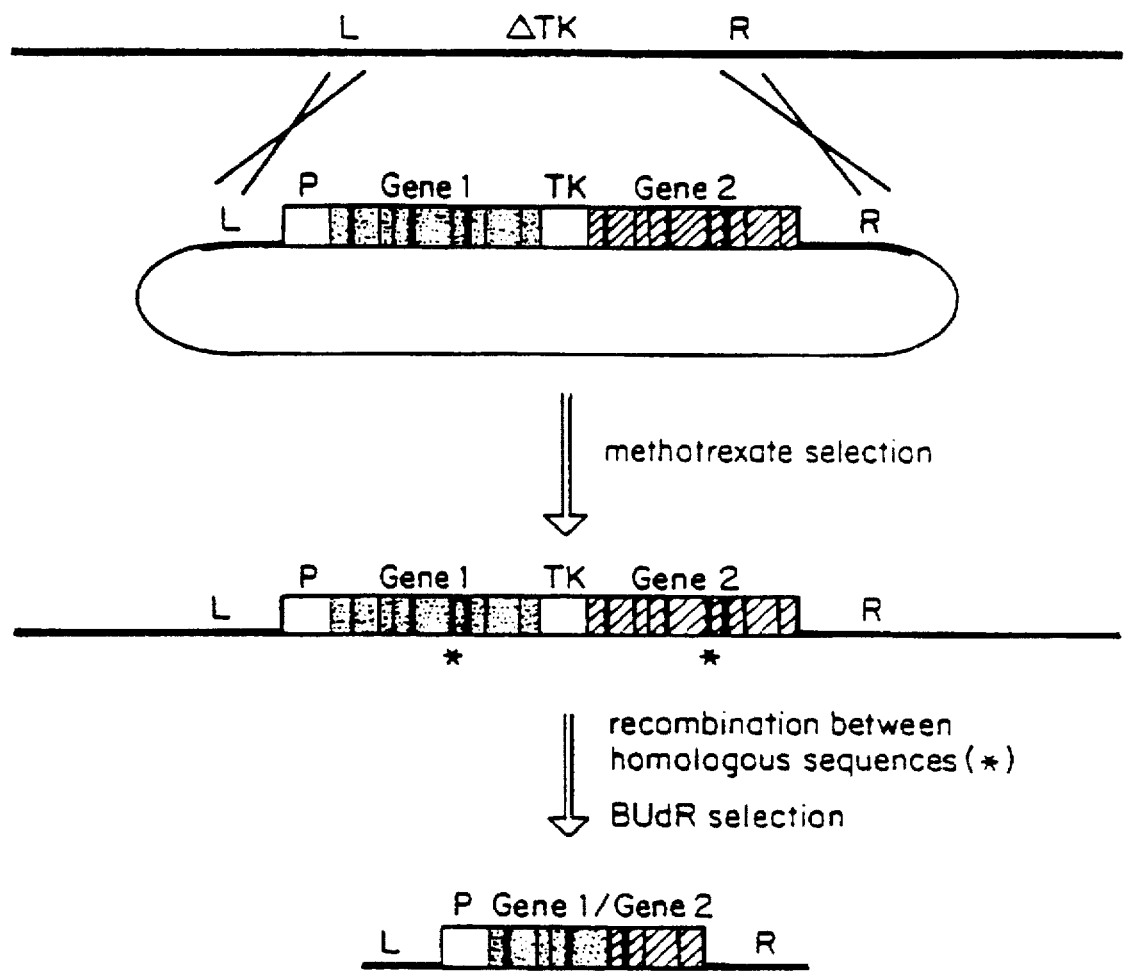

The above and various other objects and advantages of the present invention are achieved by methods for the generation, in vivo, of hybrid DNA structures from two related but different DNA sequences through various genetic recombination events within or between vital genomes, and the expression of the hybrid genes created by these methods in recombinant viruses.

1. DNA Sequences Useful for Generation of Hybrids

DNA sequences suitable for use in methods of this invention can be any two or more DNA sequences that share regions of homology (i.e., regions of similar DNA sequence). They can include DNA sequences encoding structural or functional components of various pathogens. The sequence homology that directs recombination between related DNA sequences may be localized to short regions of nucleotide identity. For example, the extent of nucleotide sequence identity necessary for intramolecular recombination in yeast can be as little as 10 nucleotides (Mazzara and Green, 1983. Abstract 116. The Molecular Biology of Yeast, Cold Spring Harbor, N.Y.). The minimum degree of homology required for intramolecular recombination between related DNA sequences can be determined experimentally for each set of related sequences.

As a particular example, it is known that the env genes encoding the envelope glycoproteins of human immunodeficiency virus (HIV), the causative agents of AIDS, vary widely among different isolates of HIV, and that each envelope glycoprotein variant elicits primarily type-specific neutralizing antibodies (i.e., antibodies capable of neutralizing only the cognate strain; Ho, D. D. et al., 1988. *Science*, 239:1021–1023). Although the nucleotide sequences of these HIV envelope genes are widely divergent, they nevertheless contain regions of DNA sequence homology suitable for the generation of hybrid genes by the methods of this invention.

In a specific embodiment, hybrid genes are generated from the env gene of the RF strain of HIV-1 and the env gene of the BH10 HIV-1 strain.

2. Host Virus

Hybrid DNA sequences can be generated in vivo in any virus (e.g., poxvirus) in which intramolecular recombination can occur between duplicated sequences. The term "intramolecular recombination" refers to recombination within a single DNA molecule as opposed to recombination between DNA molecules. In particular, this term is used herein to mean recombination within the genomic DNA of a virus.

The preferred virus used in the methods of this invention is the pox virus, vaccinia virus. The virus has been developed as an infectious eukaryotic cloning vector (Paoletti and Panicali, U.S. Pat. No. 4,603,112) and recombinant vaccinia virus has been used successfully as a vaccine in several experimental systems. The virus is considered non-oncogenic, has a well-characterized genome, and can carry large amounts of foreign DNA without loss of infectivity (Mackett, M. and G. L. Smith. 1986. *J. Gen. Virol.*, 67:2067–2082).

3. Generation of Recombinant Viruses that Contain Tandemly Arranged, Related DNA Sequences Inserted in the Genome The generation of recombinant viruses (e.g., vaccinia viruses) that contain tandemly-arranged and related DNA elements inserted in the genome is based on the following methods. Briefly, to produce the recombinant viruses, donor plasmids are constructed that contain elements to be inserted into the viral genome. These elements are flanked by DNA sequences homologous to DNA sequences present in the genome of the host virus; these sequences will serve to direct insertion of the elements to a particular region of the viral genome by in vivo recombination. Cells are infected with virus (e.g., vaccinia virus) and the infected cells are also transfected with the donor plasmids. Homologous recombination between plasmid DNA and virus DNA results in the formation of recombinant viruses that incorporate the desired elements from the donor plasmid. Various virus selection schemes (e.g., see Spyropoulos et al., 1988. *J. Virol.* 62:1046–1054; Falkner and Moss. 1988. *J. Virol.* 62:1849–1854; Franke et al., 1985. *Mol. Cell Biol.* 5:1918–1924) can be incorporated into this general approach, in order to permit the identification and isolation of recombinant viruses. Specific details of two approaches used in this invention are described below.

a. Donor Plasmids for in Vivo Recombination with Host Virus

In the first approach (FIG. 1), tandemly arranged related genes are inserted into the genome of the virus (e.g. vaccinia virus) in a single recombination event by means of a specially designed donor vector.

A preferred donor vector contains (in a 5' to 3' orientation):

i) a transcriptional promoter;

ii) a first gene or gene fragment, encoding a polypeptide of interest, under the control of the Transcriptional promoter;

iii) a gene encoding a selectable marker, also under the control of a transcriptional promoter;

iv) a second gene or gene fragment containing region(s) of DNA sequence homologous to the first gene, encoding a second polypeptide of interest.

The preferred donor vector also contains viral DNA sequences (labeled L and R in FIG. 1) flanking the construct of elements i–iv, the flanking segments being homologous to a region of the vital genome into which the tandem genes are to be inserted.

The transcriptional promoters in i and iii are required for the expression of the adjacent genes in vivo. For vaccinia virus, for example, these may include any of the well-characterized and isolated transcriptional promoters, such as the 7.5K promoter (Venkatesan et al. 1981 *Cell* 25:805–813); the BamF promoter (Panicali et al. 1983 *Proc. Natl. Acad. Sci. USA* 80:5364–5368); the 40K promoter (Rosel et al. 1986. *J Virol.* 60:436–449); the 30K promoter (Perkus et al. 1985 Science 229:981–984); the tk promoter (Hruby et al. 1983 *Proc. Natl. Acad. Sci. USA* 80:3411–3415) and the 11K promoter (Bertholet et al. 1985 *Proc. Natl. Aced. Sci. USA* 82:2096–2100).

The gene encoding the selectable marker (element iii) is required for the maintenance of the tandemly duplicated structure during viral replication. Several types of marker genes can be used. A particularly preferred marker gene is the gene encoding thymidine kinase (tk). Viruses that contain this gene can grow in the presence of the chemical methotrexate, while viruses lacking this gene cannot (Complone-Piccardo et al., 1979. *J. Virol.* 31:281–287). Thus, recombinants that contain the tk gene can be selected on the basis of their ability to grow in methotrexate.

Other selectable markers include the vaccinia virus host range (29K) gene (Gillard et al., *Proc. Natl. Acad. Sci. USA.* 83:5573–5577 1986), or genes that confer chemical or antibiotic resistance, such as the *E. coli* Neo$^R$ or gpt genes (Franke et al., Mol. Cell. Biol. 5:1918–1924 1985; Falkner and Moss. 1988. *J. Virol.* 62:1849–1854 1988).

In the second approach (FIG. 2), tandemly arranged related genes are inserted into the viral genome via two separate and sequential recombination events. A first gene, under the control of a transcriptional promoter, is inserted into the viral genome using standard techniques of in vivo recombination. The second related gene, together with a gene encoding a selectable marker (e.g., thymidine kinase) is then inserted into the virus containing the first gene. This insertion occurs via recombination between the first gene, contained on the vital genome, and the second gene, contained on a donor plasmid. This second recombination event generates a virus that contains two hybrid genes in tandem; these genes are separated by a gene encoding the selectable marker.

In this second approach, the donor plasmid vector for inserting a second, related gene into a virus that already contains a first related gene has the following elements:

i) a gene or gene fragment containing one or more regions homologous to a first gene already present in the genome of a recombinant virus; and ii) a gene encoding a selectable marker, under the control of a transcriptional promoter.

A preferred marker gene is the tk gene, as described previously.

b. Integration of Foreign Sequences into the Viral Genome and Isolation of Recombinants As described briefly above, homologous recombination between donor plasmid DNA and virus DNA in an infected cell results in the formation of recombinant viruses that have incorporated the desired elements. Appropriate host cells for in vivo recombination are generally eukaryotic cells that can be infected by the virus (e.g., vaccinia virus) and transfected by the plasmid vector. Examples of such cells are chick embryo fibroblasts, HuTK143 (human) cells, and CV-1 and BSC-40 (both monkey kidney) cells. Infection of cells with vaccinia virus and transfection of these cells with plasmid vectors is accomplished by techniques standard in the art such as Panicali and Paoletti, U.S. Pat. No. 4,603,112, incorporated by reference herein.

In both of the approaches described above, selection for function of the marker gene (e.g., the tk gene) following in vivo recombination permits isolation of recombinants that contain tandemly arranged and related genes (i.e., genes that share regions of DNA homology). Both approaches (FIGS. 1 and 2) will yield recombinant viruses in which the marker gene is positioned between the two tandemly arranged and related genes.

4. Intramolecular Recombination

Methods of this invention for generating hybrid genes from two related genes in a recombinant virus are based upon the genetic instability of tandemly arranged non-identical DNA sequences that share regions of homology. Intramolecular recombination between regions of homology shared by the two related genes, which occurs during the course of normal viral replication, results in the formation of a single hybrid gene composed of portions of the two original genes. Because the recombination events can occur randomly between any homologous sequences contained on the two genes, these events will generate a spectrum of hybrid genes.

In viruses generated by approach 1 or approach 2 (FIGS. 1 and 2, respectively), a gene encoding a selectable marker resides between the two tandemly arranged related genes. This arrangement permits isolation and propagation of viruses containing the genetically unstable tandem gene arrangement. Viruses are propagated under conditions that permit growth of only those recombinants that contain the marker gene.

Intramolecular recombination between homologous sequences on the two tandemly arranged, related genes results in the excision of the marker gene. Viruses that have undergone intramolecular recombination to generate a hybrid gene can be identified, and in some cases, selected for, by virtue of the lack of the function encoded by the now-absent marker gene. For example, when the tk gene is used as the selectable marker, those progeny viruses that have undergone intramolecular recombination, with the concomitant excision of the tk gene, can be selected in a medium containing 5-bromo-2'-deoxyuridine (BUdR) or trifluorothymidine. In this selective medium, only those viruses which lack tk gene function can survive.

In viruses generated by approach 1, intramolecular recombination between tandemly arranged, related genes will yield a final hybrid gene that contains a single fusion junction, i.e., the 5' portion of the hybrid gene will be derived from the 5' region of one of the two original genes, while the 3' portion of the hybrid gene will be derived from the 3' region of the second of the two original genes. Each individual hybrid gene will contain a different fusion junction, generated by random recombination between the homologous regions shared by the two original genes (FIG. 1).

In viruses generated by approach 2, each of the tandemly arranged genes is itself a hybrid gene, formed by recombination between a first gene located in the viral genome and a second, related gene contained on the donor plasmid.

Figure 2:
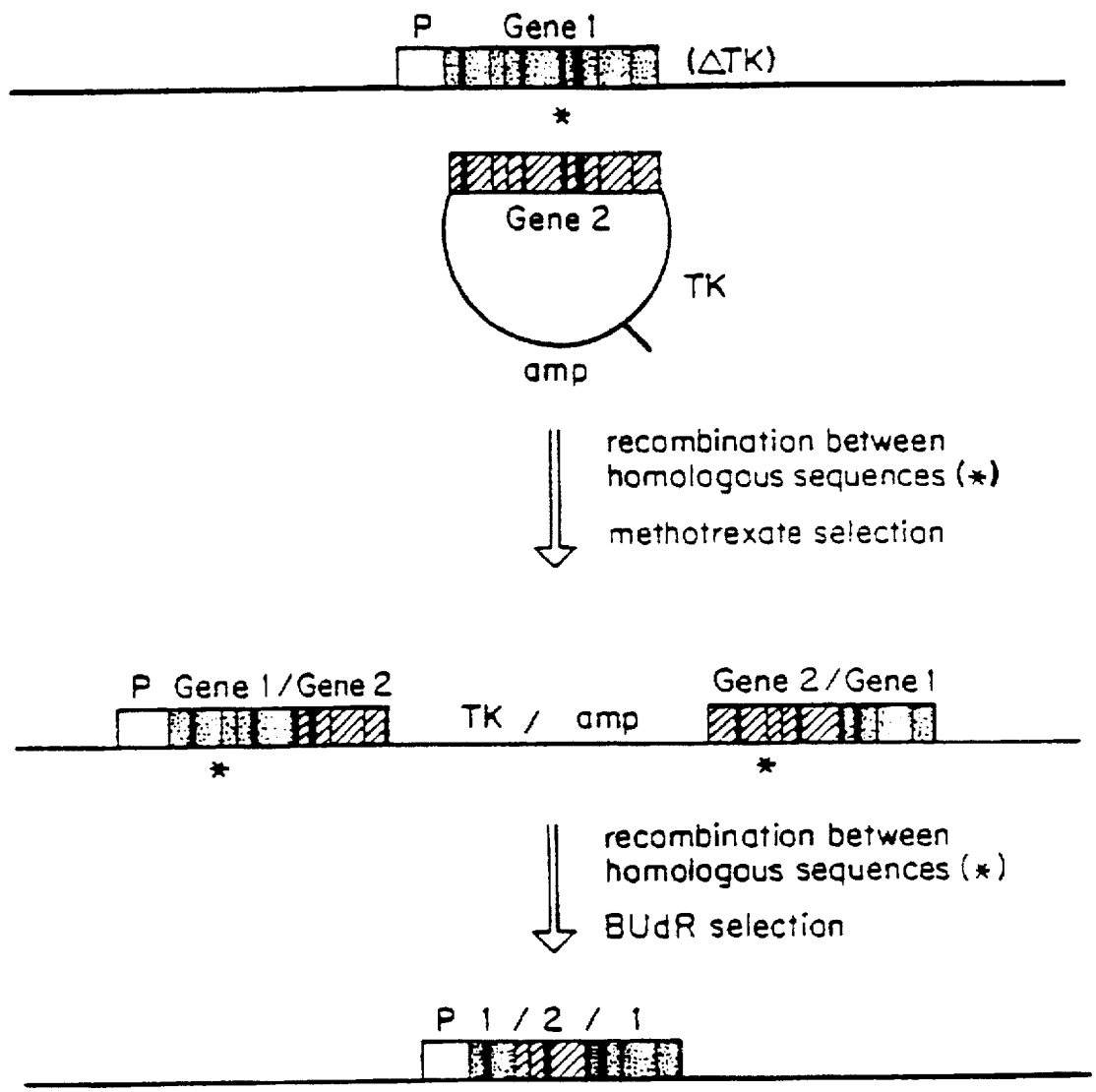

Intramolecular recombination between this pair of hybrid genes results in the formation of a single hybrid gene that contains two separate fusion junctions. Thus, the final hybrid gene will contain 5' and 3' segments from one of the two original genes flanking a center segment derived from the second of the two original genes (FIG. 2).

5. Recombinant Virus as Vaccines

The methods of this invention can be exploited to produce a vaccine in the form of live, recombinant viral vectors capable of expressing a unique chimeric protein, or a population of related chimeric proteins or protein segments, from a pathogenic organism that exhibits antigenic variation. A recombinant virus (e.g., poxvirus) that contains tandemly arranged genes encoding antigenically distinct forms of a chosen polypeptide can serve as the progenitor of a population of progeny viruses, each of which contains a different hybrid gene composed of portions of the original tandemly arranged genes. These hybrid genes, created by intramolecular recombination events, can be expressed by the recombinant poxviruses as chimeric polypeptides.

If the chimeric polypeptides represent an immunologically important antigen of a pathogenic organism (e.g., the HIV env antigen), particularly an organism that exhibits antigenic and genomic variation, the population of viral vectors that express these polypeptides may be used as live recombinant vaccines; these vaccines may elicit immune responses to a broad range of serological types and subtypes of the pathogen.

As an alternative to the use of the whole population of progeny viruses containing hybrid genes, it is also possible to isolate individual members of the population, each of which expresses a different and unique hybrid gene. The individual, plaque purified recombinants can be examined for their potential to elicit immune responses to the several variants of the cognate pathogen; appropriate recombinants can then be used, individually or in combination, to formulate a live recombinant vaccine.

An example of the use of the methods of this invention is the development of a vaccine effective against multiple strains of the human immuno-deficiency viruses, HIV-1 and HIV-2, the causative agents of AIDS. The genetic and antigenic variation among strains of HIV, which resides primarily in the genes encoding the vital envelope proteins, presents a major obstacle to the development of an HIV vaccine, as a vaccine effective against one variant may fail to protect against related strains. To generate a vaccine with potential for eliciting an immune response against multiple HIV strains, a parental poxvirus that contains, tandemly arranged in the genome, envelope genes from two widely divergent HIV-1 strains (e.g., the RF and BH10 strains) can be constructed. Intramolecular recombination between homologous regions of the two HIV envelope genes in the parental virus will give rise to a population of progeny viruses, each of which contains a unique hybrid envelope gene generated from the random recombination between homologous regions shared by the two original genes. The chimeric envelope proteins encoded by these hybrid genes will contain both novel combinations of epitopes as well as new discontinuous epitopes. Either individual members of this population, a mixture of selected members of this population, or the entire population of progeny viruses can be used as a vaccine to immunize persons susceptible to HIV infection. During replication of the progeny viruses in an immunized host, the chimeric antigens will be expressed along with the normal complement of poxviral genes. These antigens will stimulate an immunological response directed against the variety of epitopes represented in the population; this immune response may be effective against a spectrum of HIV stains.

A number of other pathogens, in addition to HIV, exhibit genetic and antigenic variation which allows them to escape host immune surveillance. These include various parasites, such as trypanosomes and malarial plasmodia; and viruses, such as influenza virus (an orthomyxovirus), certain picornaviruses, and retroviruses. The methods of this invention may be applied to the development of a vaccine for any of these pathogens.

6. The Generation of Chimeric Proteins for Pharmaceutical Uses

Although the methods of this invention are particularly suitable for developing vaccines against pathogens which exhibit antigenic diversity, they can also be used to generate hybrid genes encoding chimeric proteins for other applications. For example, a recombinant virus that contains, tandemly arranged in the viral genome, genes encoding related interferons (or any two related genes encoding pharmacologically important polypeptides) will, upon Intramolecular recombination, give rise to progeny viruses that contain hybrid genes. Individual progeny viruses generated by the recombination events could be isolated and the chimeric proteins synthesized by these viruses could be purified and examined for the desired novel biological properties. Alternatively, the novel hybrid genes contained in the individual progeny viruses could be isolated by standard recombinant DNA methodologies and expressed in alternate recombinant organisms, including *E. coli*, yeast, baculovirus, or eukaryotic cells.

7. The Generation of Chimeric Proteins for Mapping

Hybrid glycoprotein genes have been used to map type-specific antigenic determinants. For example, a large number of hybrid genes containing portions of the glycoprotein genes from vesicular stomatitis virus serotypes Indiana and New Jersey were made by standard techniques of recombinant DNA. These hybrid genes were individually expressed in vaccinia virus and were used to map antigenic determinants recognized by type-specific monoclonal antibodies (Keil and Wagner, 1989 Virology 170:392–407).

The methods of this invention can also be used to map type-specific antigenic determinants. For example, given two related proteins and a collection of type-specific antibodies which recognize only one (or the other) of the two proteins, the epitope recognized by each antibody can be mapped by constructing a recombinant virus containing the two related genes. The resulting intramolecular recombination events between the two related genes will generate a population of viruses containing a spectrum of hybrid genes. Antibody binding to individual hybrid proteins can then be assayed (for example, by black plaque assay on the viral population). The genes encoding individual hybrids of interest can then be mapped (for example, using the polymerase chain reaction technique to amplify the hybrid gene in the viral genome, followed by restriction mapping or sequence analysis) to localize the epitope.

The invention is illustrated further by the following Exemplification.

EXEMPLIFICATION

Cells and Virus

*E. coli* strains JM101 (Messing et al., *Nucl. Acids Res.*, 9:309 (1981)) and MC1061 (Casadaban and Cohen, *J. Mol. Biol.*, 138:179 (1980)) can be used as the host for the growth of all plasmids. The monkey kidney cell line BSC-40 is used for vaccinia virus infections. Vaccinia virus tk- mutant WR 417 (Spyropoulos et al., *J. Virol.*, 62:1046–1054 (1988)) is used as the parental virus for in vivo recombination.

Enzymes

Restriction enzymes are obtained from New England BioLabs or Boehringer-Mannheim. The large fragment of DNA polymerase (Klenow) is obtained from United States Biochemical Corp. calf intestinal phosphatase (CIP) and T4 DNA ligase is obtained from Boehringer-Mannheim.

Molecular Cloning Procedures

Restriction enzyme digestions, purification of DNA fragments and plasmids, treatment of DNA with CIP, Klenow, ligase or linkers and transformation of E. coli are performed essentially as described (Maniatis et al., Molecular Cloning: A Laboratory Manual, Cold Spring Harbor Laboratory, Cold Spring Harbor, N.Y., 1982), incorporated herein by reference.

Preparation of Vaccinia Virus Recombinants

Viral infection, transfections, plaque purification and virus amplification are performed essentially as described (Spyropoulos et al., J. Virol., 62:1046–1054 (1988)). Infection and transfection were performed in the presence of 5 uM methotrexate (MTX); plaques were plated and purified in the absence of MTX.

Vaccinia Virus Genomic Analysis

DNA is extracted from vaccinia virus-infected cells as described (Esposito et al., J. Virol. Methods, 2:175 (1981)) and analyzed by restriction enzyme digestions and Southern hybridization as described (Mantatis et al., Molecular Cloning: A Laboratory Manual, Cold Spring Harbor Laboratory, Cold Spring Harbor, N.Y., 1982). Vaccinia virus recombinant DNA is subcloned into phage m13mp18 (New England Biolabs) and sequenced by the chain-termination method (Sanger et al., Proc. National Acad. Sci. USA, 74:5463 (1977)). Polymerase chain reaction was performed using a kit (Perkin Elmer Cetus) according to manufacturer's instructions.

Anti-vaccinia ELISA

A vaccinia virus antigen preparation was made by infecting BSC40 cells with NYCBH at a multiplicity of 1 for 24 hours. The infected cells were harvested in 1 mM Trts, pH 9.0. This lysate was diluted in coating buffer (50 mM $NaHCO_3$, pH 9.6) to a concentration of 10 μg/ml total protein and was used to coat microtiter plates (Maxisorp Immunoplate, Nunc) for 2 hours at 37° C. Following aspiration of the lysate, serum samples from immunized rabbits were added to the plates, and serially diluted in Blotto (3% dry milk, 2% normal goat serum, 0.1% Tween-20, in PBS, pH 7.3). They were incubated for 16 hours at 4° C., washed three times, and then incubated for 1 hour at 37° with horseradish peroxidase-labeled goat anti-rabbit IgG (H+L) (Jackson Immunoresearch, West Grove, Pa.) diluted 1:5000 in Blotto. Plates were washed again three times, and the reaction was developed for 5 minutes using 0.2 mg/ml TMB (tetramethylbenzidine; Sigma, St. Louis, Mo.) in 0.1M acetate buffer, pH 6.0. The reaction was stopped by the addition of 2.5N $H_2SO_4$, and the resulting color read at 450 nm. Titers were defined as the dilution of serum which gave an OD equal to one-half the maximum reaction obtained with a positive control mouse serum.

Western Blot Analysis

Epiblot™ strips (Organon Teknika, Jessup, Md.) were incubated at room temperature for 1 hour with rabbit serum diluted 1:500 in Blotto. Strips were washed 3 times for 5 minutes with Blotto, and were then incubated for 1 hour at room temperature with alkaline phosphatase labeled goat anti-rabbit IgG (H+L) (Kirekegaard and Perry Labs (KPL) Gaithersburg, Md.) diluted 1:1000 in Blotto. The strips were washed once with Blotto, and twice with High Salt Wash buffer (500 mM NaCl, 20 mM Tris, 0.5% Tween-20, pH 7.4), and the reaction developed with a BCIP/NBT substrate kit (KPL). HIV-1 bands were identified by comparison with a strip developed using a human $HIV^+$/vaccinia$^-$ control serum.

HIV Neutralization Assay

In this assay, a modification of that described by Weiss et al. (Nature 324:572–575.; 1986), 100 ul aliquots of HTLV-IIIB virus suspension containing 100 TCID50 (as determined by previous titrations on c8166 cells) were incubated with equal volumes of rabbit antisera serially diluted in RPMI with 10% FCS for one hour at 37° C. Duplicate 100 ul samples of virus-serum suspension are then inoculated onto 100 ul cell suspension containing $1 \times 10^5$ c8166 cells in RPMI 1640 with 10% FCS in the wells of flat bottom 96 well plates. Plates are then incubated in humidified, 5% $CO_2$ environment at 37° C. Appropriate viral controls are used to ensure the accuracy of the initial viral inoculum. At day four, the number of centers of syncytia per well are counted and supernatants are assayed for HIV p-24 by Dupont EIA. The neutralization titer is defined as that serum dilution which produces a 90% decrease in centers of syncytia and p-24 production.

Products and compositions described herein are hybrid proteins derived from the expression of condensed genes contained within viruses that have undergone intramolecular recombination according to the methods of the present invention. These proteins can have antigenic properties and, when suitably expressed, may serve a variety of purposes. One such use can be proteins that elicit immune responses to a broad range of HIV isolates. Particular compositions of this invention are chimeric env genes containing combined sequences of the RF and BH10 env genes of HIV-1.

This invention will now be more specifically characterized through the use of the following examples, which are not construed to be limiting.

EXAMPLE 1

Construction of a plasmid containing the HIV strain BH10 env gene fused to the E. coli lacZ gene, under the control of the vaccinia 7.5K promoter (FIG. 3)

Figures 3A, 3B:
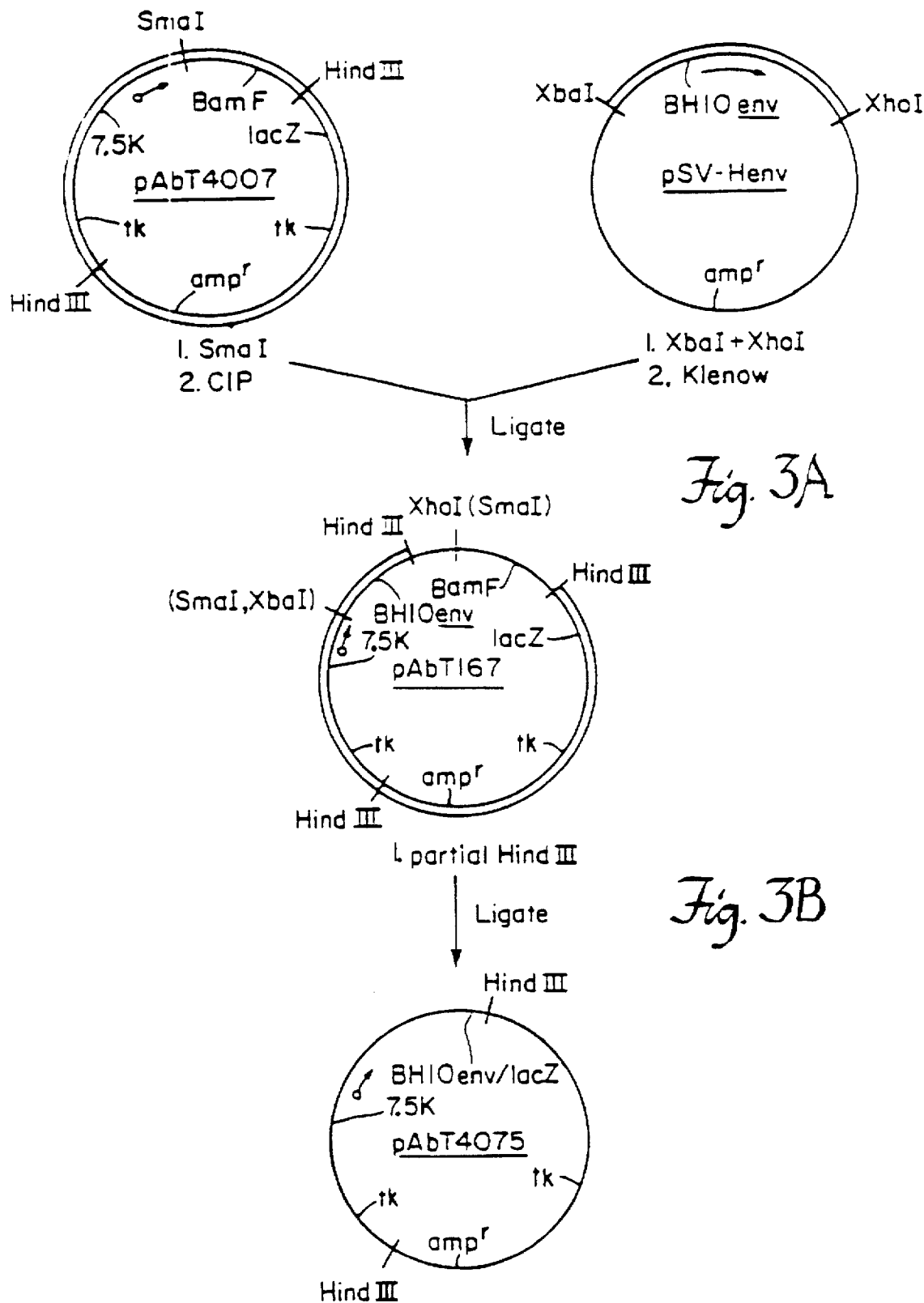

The HIV-1 strain BH10 env gene is located on plasmid pSV-Henv, obtained from Blair Ferguson (E.I. DuPont deNemours and Co.). pSV-Henv was digested with XbaI and XhoI, treated with Klenow, and the 2700 bp fragment containing the env-encoding sequence was gel-purified. pAbT4007 (See U.S. patent application Ser. No. 910,501, filed Sep. 23, 1986) was digested with SmaI, treated with CIP, and ligated to the 2700 bp fragment to create pAbT167, as shown in FIG. 3A.

pAbT167 was partially digested with HindIII, and a 9500 bp partial digestion product, lacking both the 3' end of the env gene and the BamF promoter, was gel-purified and self-ligated to form pAbT4075 as shown in FIG. 3B. pAbT4075 contains the BH10 env gene fused in-frame to lacZ at the HindIII site at position 2000 in the BH10 env gene, encoding all of env protein gp120 and approximately 300 bp of env protein gp41.

EXAMPLE 2

Figure 4A:
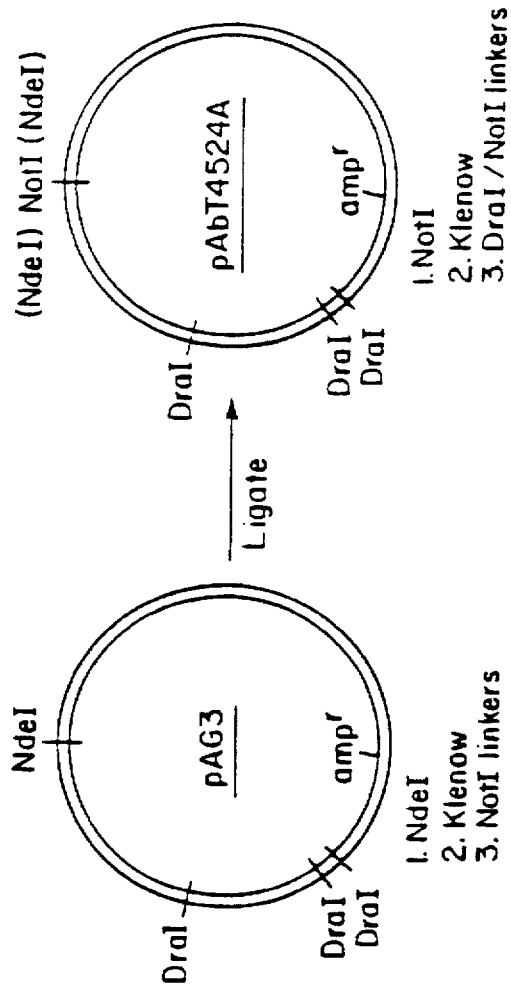
Figure 4B:
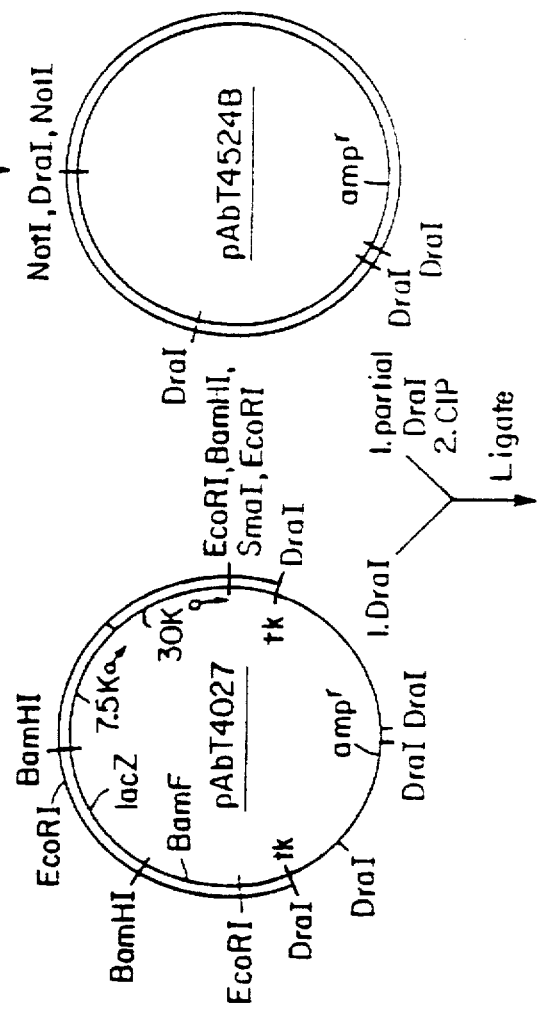
Figure 4C:
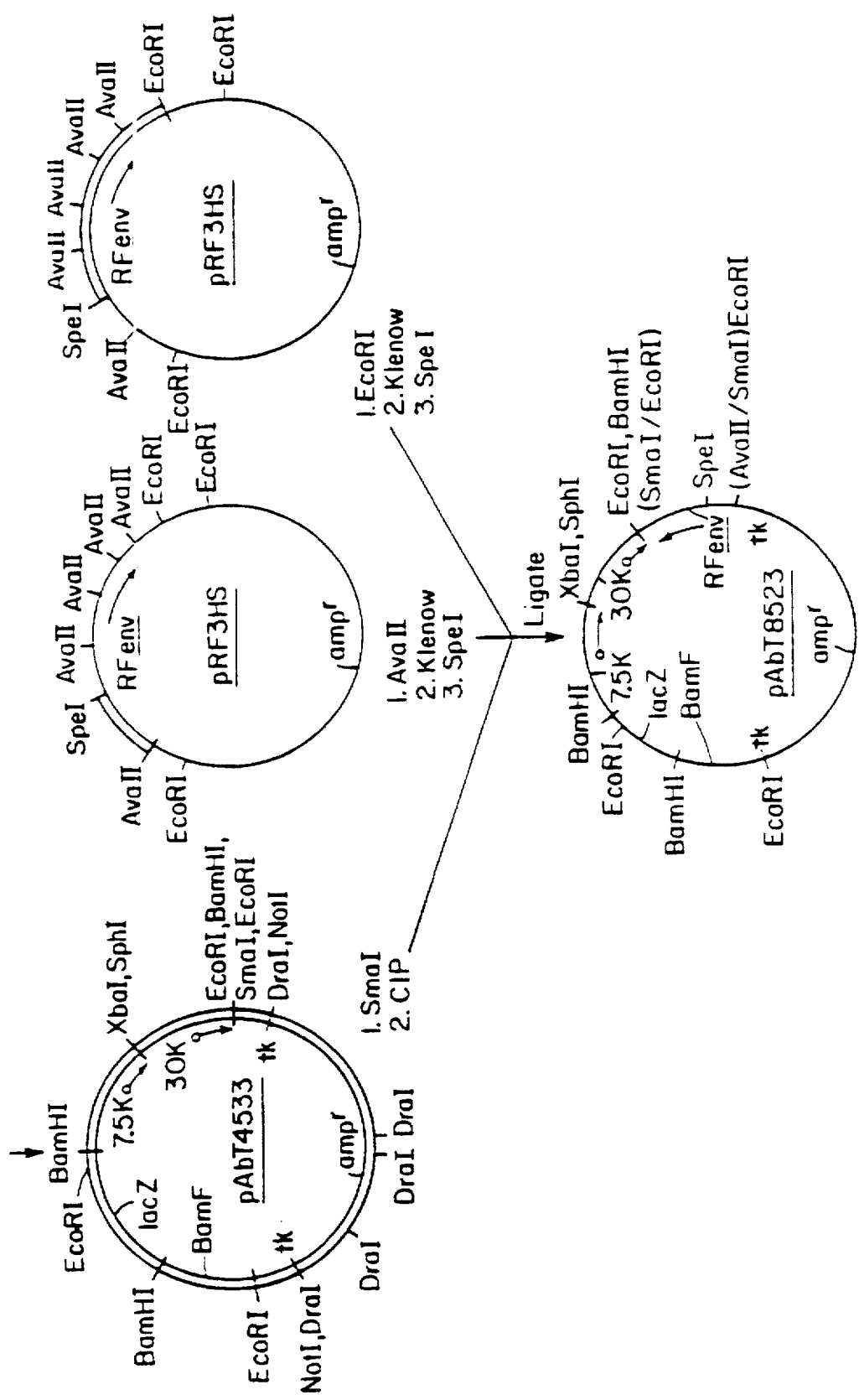
Figure 5A:
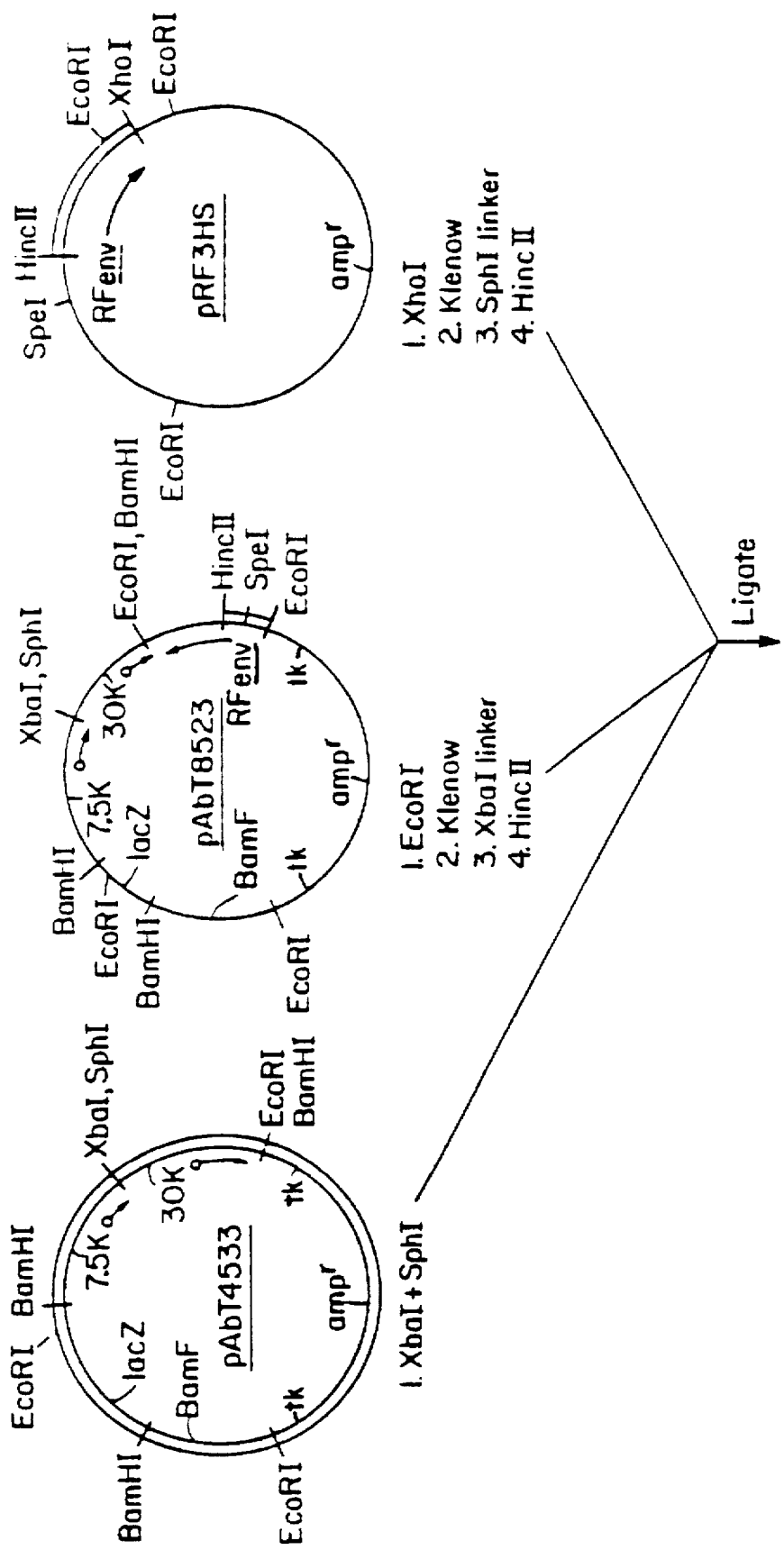
Figure 5B:
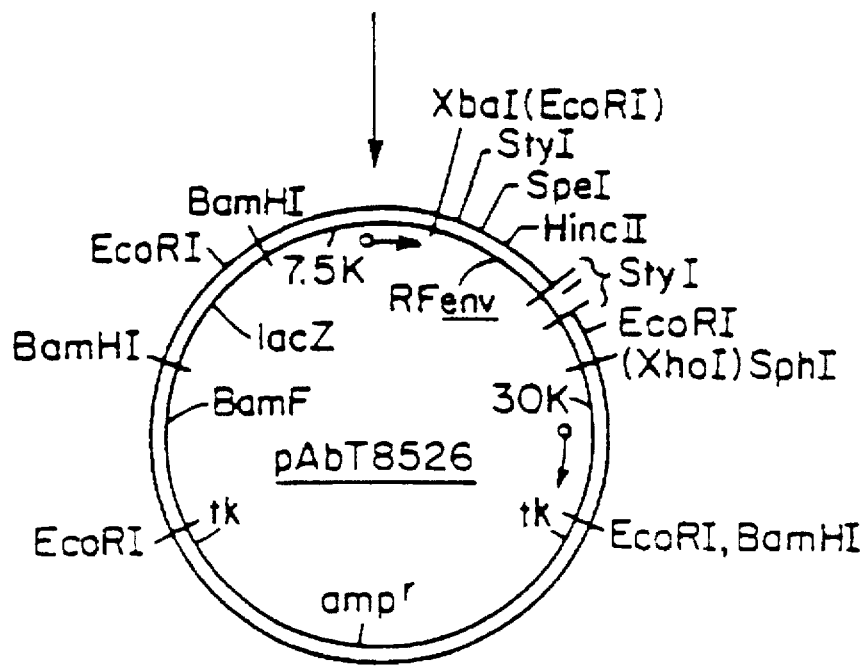
Figure 5B:
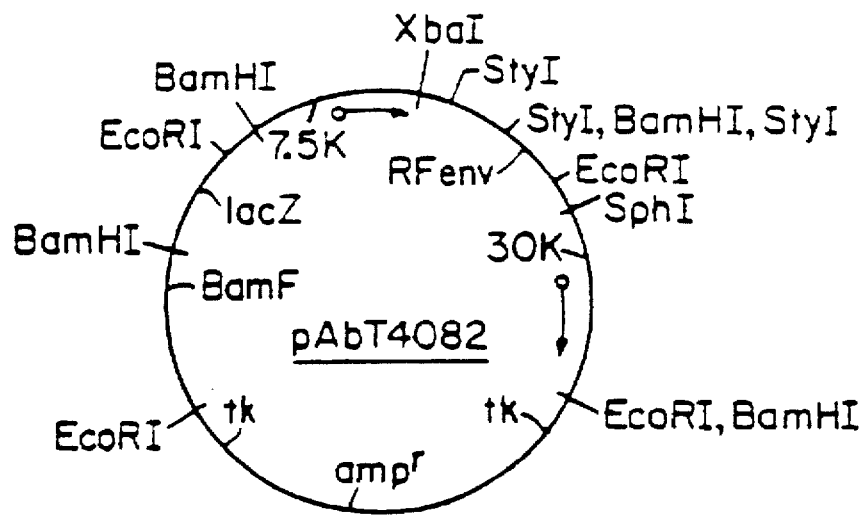

Construction of a plasmid containing the HIV strain RF env gene modified at the 5' end of the gp41-encoding portion of the gene (FIGS. 4, 5)

pAG3 (U.S. Pat. No. 5,242,829 supra) was digested with NdeI, treated with Klenow, and ligated to NotI linkers (dGCGGCCGC; New England BioLabs). The resulting plasmid, pAbT4524A, was digested with NotI, treated with Klenow and ligated to a synthetic oligonucleotide (dGCTTTAAAGC; Biology Department, Brandeis University), containing a DraI site and restoring NotI sites flanking the DraI site in plasmid pAbT4524B, as shown in FIG. 4A.

pAbT027 (U.S. Pat. No. 5,242,829) was digested with DraI and a 5530 bp fragment was gel-purified. pAbT4524B was partially digested with DraI. A 2260 bp fragment was gel-purified, treated with CIP and ligated to the 5530 bp fragment to create pAbT4533, as shown in FIG. 4B.

The HIV-1 strain RF env gene was obtained on plasmid pRF3HS from Blair Ferguson (E.I. DuPont deNemours and Co.). pRF3HS was digested with AvaII, treated with Klenow, digested with SpeI and the resulting 500 bp fragment containing the 5' end of the RF env gene was gel-purified. pRF3HS was digested with EcoRI, treated with Klenow, digested with SpeI and the resulting 2100 bp fragment containing the 3' end of the RF env gene was gel-purified. pAbT4533 was digested with SmaI, treated with CIP and ligated to the 500 bp and 2100 bp fragments to create pAbT8523, as shown in FIG. 4C.

pAbT8523 was digested with EcoRI, treated with Klenow, ligated to an XbaI linker (New England Biolabs), digested with HincII, and a 900 bp fragment containing the 5' end of RF env was gel-purified. pRF3HS was digested with XhoI, treated with Klenow, ligated to an SphI linker (New England Biolabs), digested with HincII and a 1700 bp fragment containing the 3' end of RF env was gel-purified. pAbT4533 was digested with XbaI and SphI and ligated to the 900 and 1700 bp fragments to form pAbT8526, as shown in FIG. 5A.

pAbT8526 was partially digested with StyI, treated with Klenow, and a 10,600 bp fragment was gel-purified and ligated to a BamHI linker (dCGGATCCG; New England Biolabs) to create pAbT4082 as shown in FIG. 5B. pAbT4082 contains the HIV-1 RF env gene with a BamHI site inserted at the StyI site at position 1600, at the 5' end of the gp41-encoding region, 30 bp 3' to the gp120-gp41 junction.

EXAMPLE 3

Figures 6A, 6B:
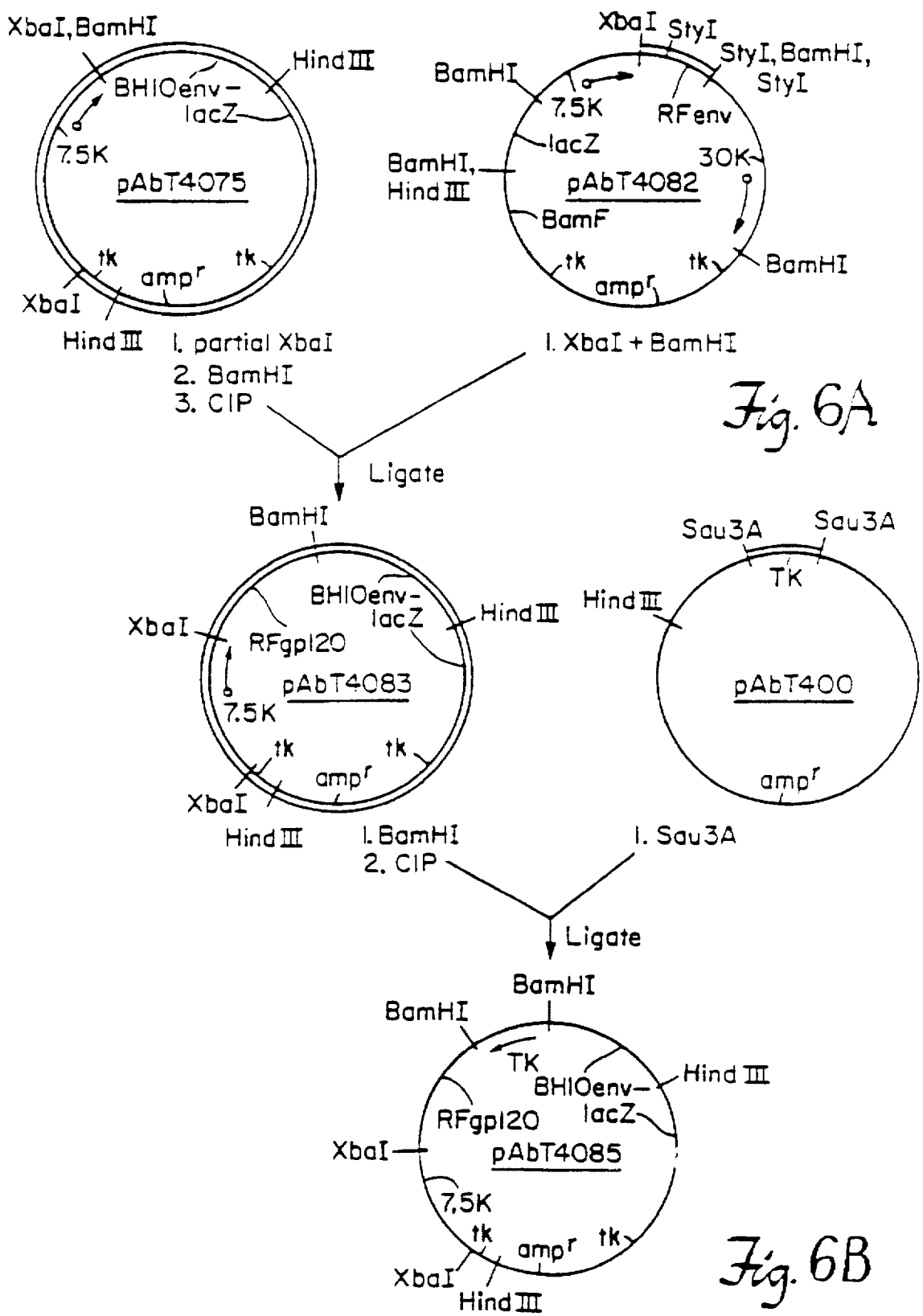
Figure 7:
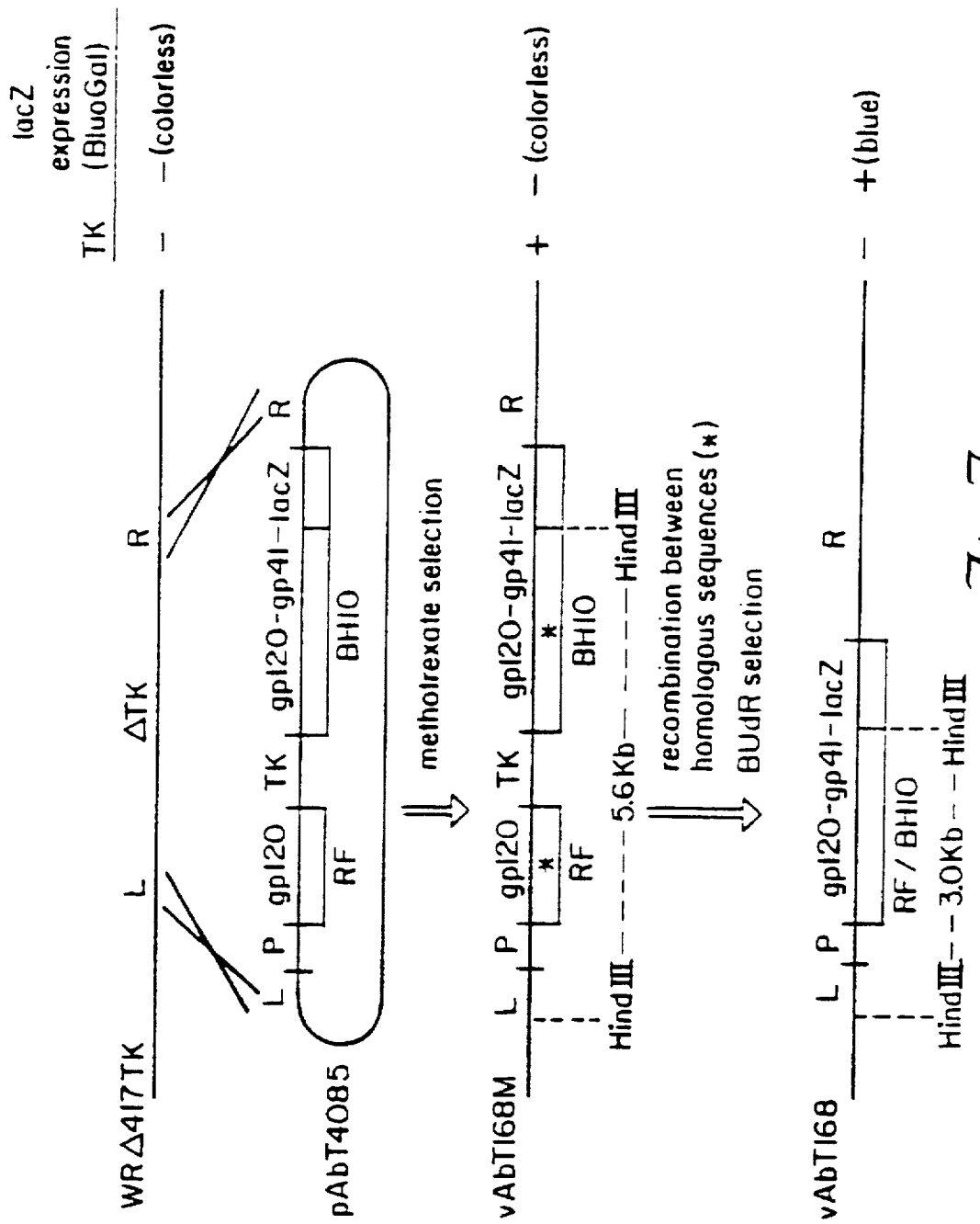
Figure 8A:
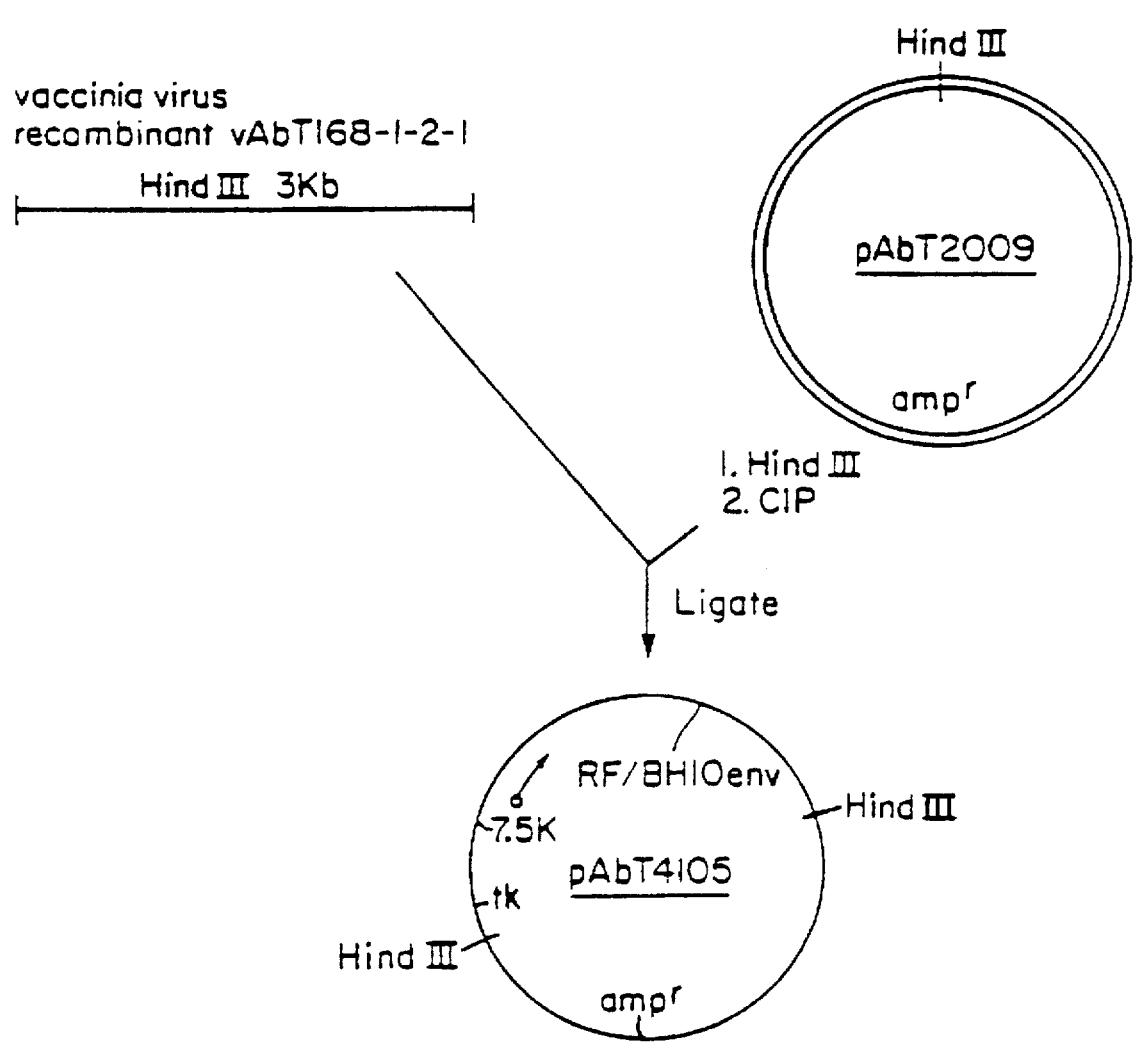
Figure 8B:
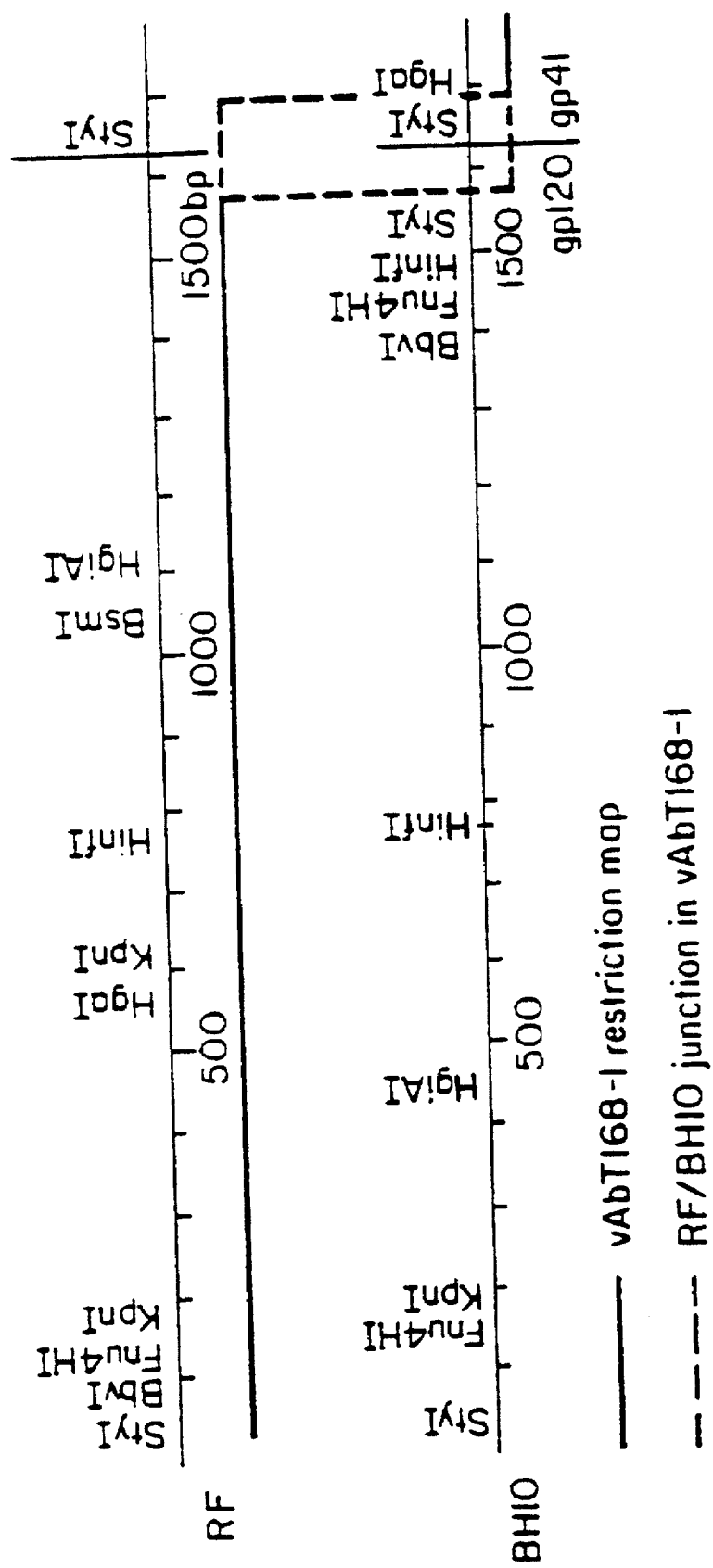

Construction of an IVR vector containing the vaccinia virus thymidine kinase gene flanked by the gp120 portion of the HIV-1 strain RF env gene and the HIV-1 strain BH10 env gene fused to lacZ (FIG. 6)

pAbT4082 was digested with XbaI and BamHI and the 1700 bp fragment containing the RF gp120 gene was gel-purified. pAbT4075 was digested with BamHI, partially digested with XbaI and treated with CIP, and a 9500 bp fragment was gel-purified and ligated to the 1700 bp fragment to create pAbT4083, as shown in FIG. 6A.

pAbT400 (U.S. Pat. No. 5,242,829) was digested with Sau3AI and the 900 bp fragment containing the vaccinia virus thymidine kinase (tk) gene was gel-purified. pAbT4083 was digested with BamHI, treated with CIP and ligated to the 900 bp fragment to create pAbT4085, as shown in FIG. 6B.

pAbT4085 contains the RF gp120, under the control of the 7.5K promoter, and the BH10 gp160 genes separated by the tk gene. In addition, the BH10 env gene is fused in-frame to the lacZ gene.

EXAMPLE 4

Figure 9A:
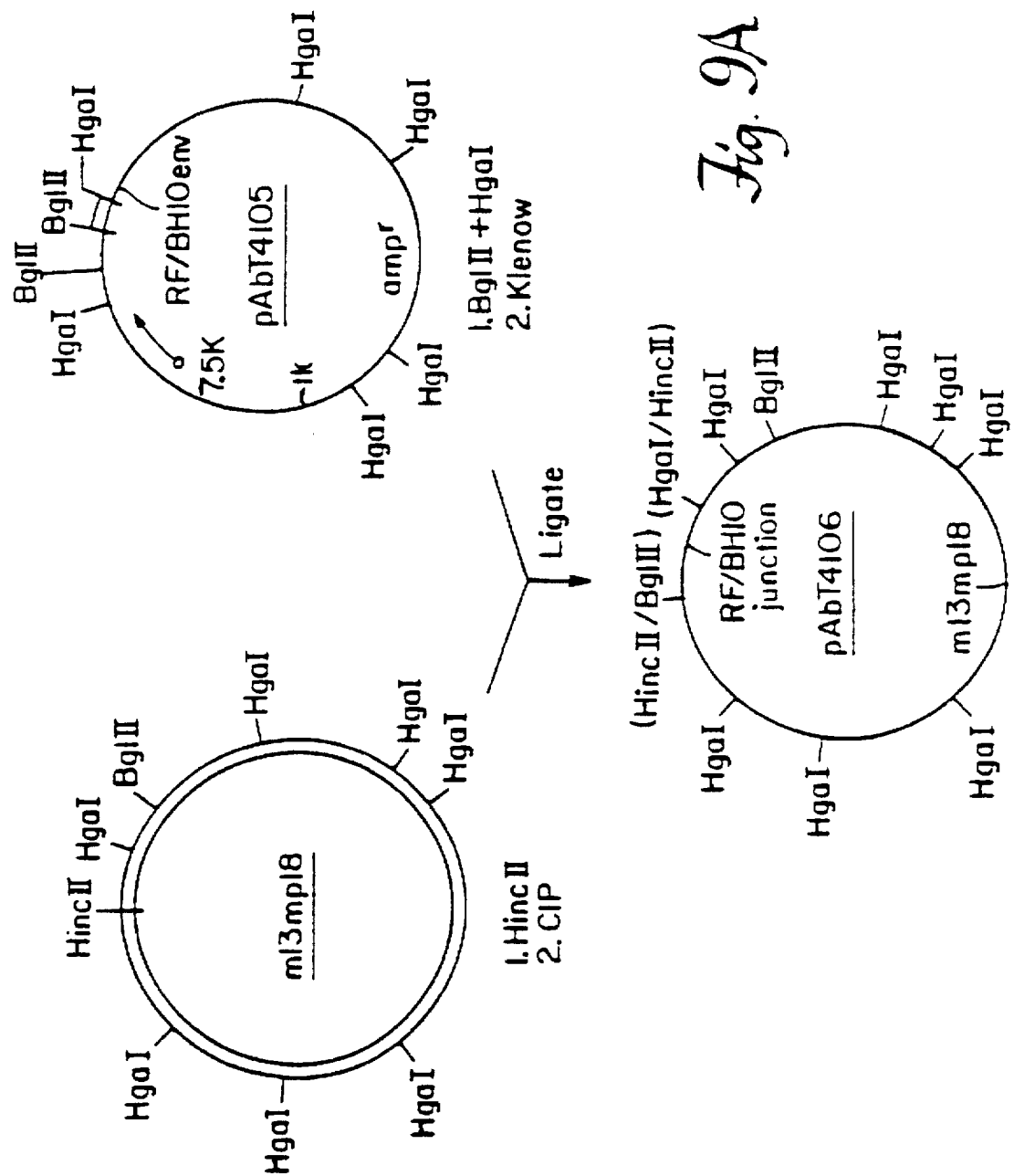
Figure 9B:
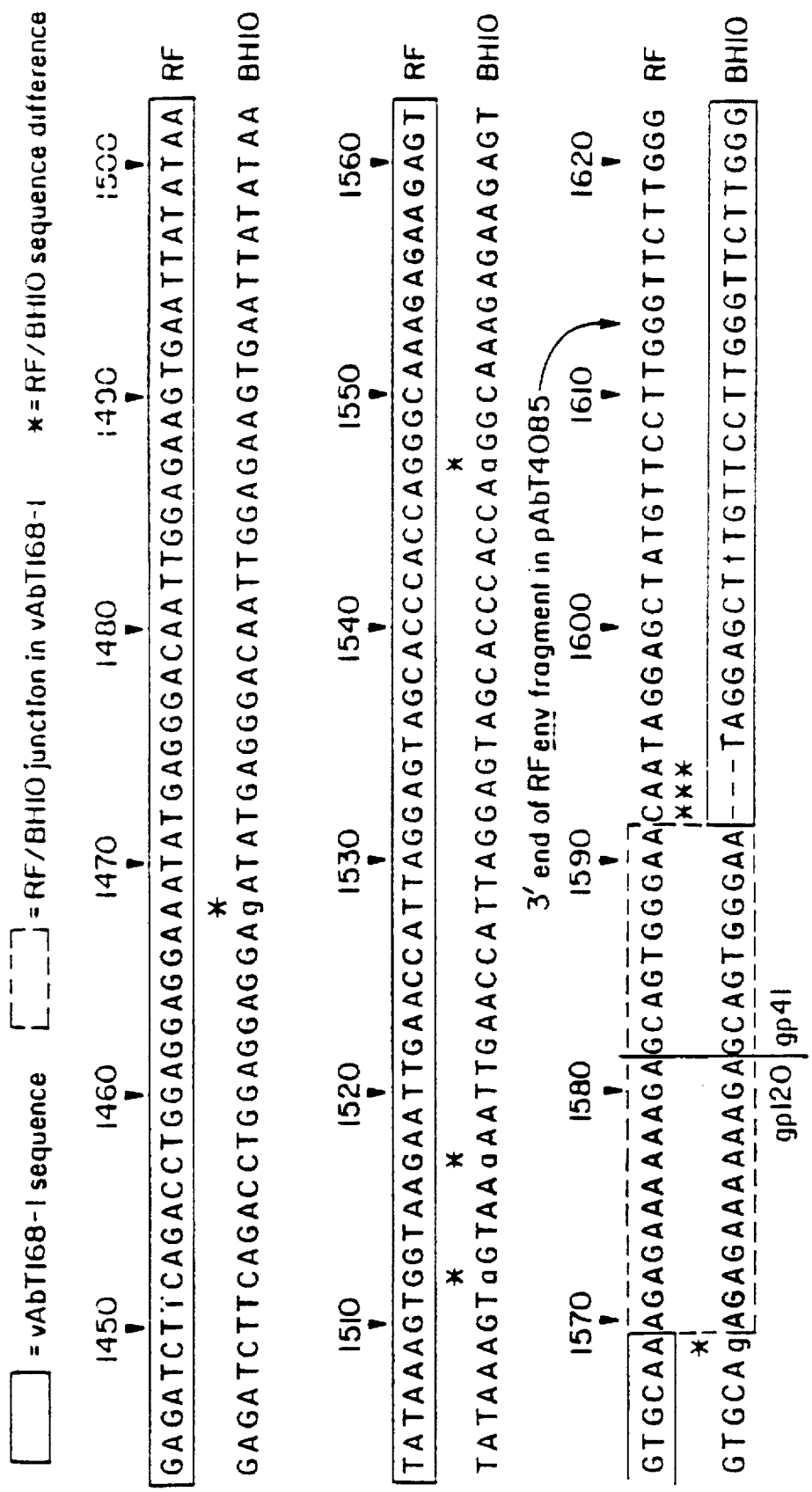

Insertion of tandem HIV-1 env gene sequences into vaccinia virus and subsequent condensation of the tandem array to yield single-copy hybrid env genes (FIG.7)

DNA sequences contained within pAbT4085 contain the tk gene flanked by two diverse env genes from HIV-1 strains BH10 and RF. These env genes differ by 21% in the amino acid sequence of their exterior envelope proteins (Starcich et al., 1986, *Cell* 45:637). This vector is used to insert the desired structure into tk vaccinia by in vivo recombination. Methotrexate is used to obtain and purify tk+ recombinants away from the parental tk$^-$ virus, which cannot grow in the presence of methotrexate. A recombinant virus is therefore generated which contains both env genes as well as the tk gene (FIG. 7).

Because recombination between conserved regions of the tandemly arrayed env genes results in deletion of the intervening sequences, including the tk gene, virus which have undergone condensation events can be selected using 5'-bromodeoxyuridine (BUdR) which permits growth of tk$^-$, but not tk$^+$, virus. As a number of conserved regions spanning the env sequence are available for recombination, a vaccinia recombinant containing two different env genes in tandem will generate a diverse set of chimeric env genes. The *E. coli* lacZ gene is included as a marker; plaques resulting from the growth of virus containing both env genes will be colorless in the presence of Xgal because there is no transcriptional promoter to express lacZ, whereas virus containing a hybrid env gene fused in-frame to lacZ will give rise to blue plaques.

Plasmid pAbT4085 was transfected into BSC-40 cells which had previously been infected with the vaccinia tk strain WR 417 (Spyropoulos et al., *J. Virol.*, 62:1046–1054 (1988)) in the presence of methotrexate. When the progeny virus population was plated in the presence of methotrexate and overlaid with Xgal only colorless (lacZ$^-$) plaques were observed. When the same population was plated in the absence of methotrexate and overlaid with Xgal, blue plaques were observed. Two blue recombinants, designated vAbT168-1 and vAbT168-2, were plaque-purified in the absence of methotrexate and amplified.

EXAMPLE 5

Analysis of the structures of two vaccinia-generated hybrid env genes fused to lacZ (FIGS. 7, 8, 9, 10)

Vaccinia virus genomic DNA was prepared from the Recombinant vAbT168-1 derived from the previous Example. The DNA was digested with HindIII and the resulting fragments separated by agarose gel electrophoresis. The restriction pattern observed was consistent with that expected for a recombinant virus which had undergone a condensation event to generate a hybrid env gene as shown in FIG. 7. A 3 kb fragment containing the putative chimeric env gene was gel-purified and ligated to pAbT2009 (U.S. Pat. No. 5,242,829, supra), previously digested with HindIII and treated with CIP, to yield the plasmid pAbT4105, as shown in FIG. 8A.

The hybrid env gene in pAbT4105 was analyzed by restriction enzyme mapping; a restriction map is shown in FIG. 8B. The results indicate that the 5' end of the hybrid env gene is derived from the RF env gene and the 3' end from the BH10 env gene. The restriction analysis localized the RF/BH10 junction to a 118 bp region between a StyI and HgaI site, as indicated in FIG. 8B.

To further define the RF/BH10 junction, pAbT4105 was digested with BglII and HgaI, treated with Klenow and a 200 bp fragment containing the hybrid junction was gel-purified. Phage m13mp18 DNA (New England Biolabs) was digested with HincII, treated with CIP and ligated to the 200 bp fragment to create pAbT4106, as shown in FIG. 9A.

Single-stranded preparations were made of pAbT4106 and the 200 bp insert sequenced by the chain-termination method. Sanger, Nicklen and Coulson, *Proc. Natl. Acad. Sci. USA*, 74, 5463 (1977). The corresponding regions of the parental RF and BH10 env genes from pAbT4085 were also sequenced. The relevant sequences of the RF, BH10 and vAbT168-1 hybrid env genes are shown in FIG. 9B. Thus the RF/BH10 condensation event occurred within a conserved 22 bp region common to both the RF and BH10 env genes, located 21–43 bp from the 3' end of the RF env fragment in pAbT4085 (FIG. 9B).

Figure 10A:
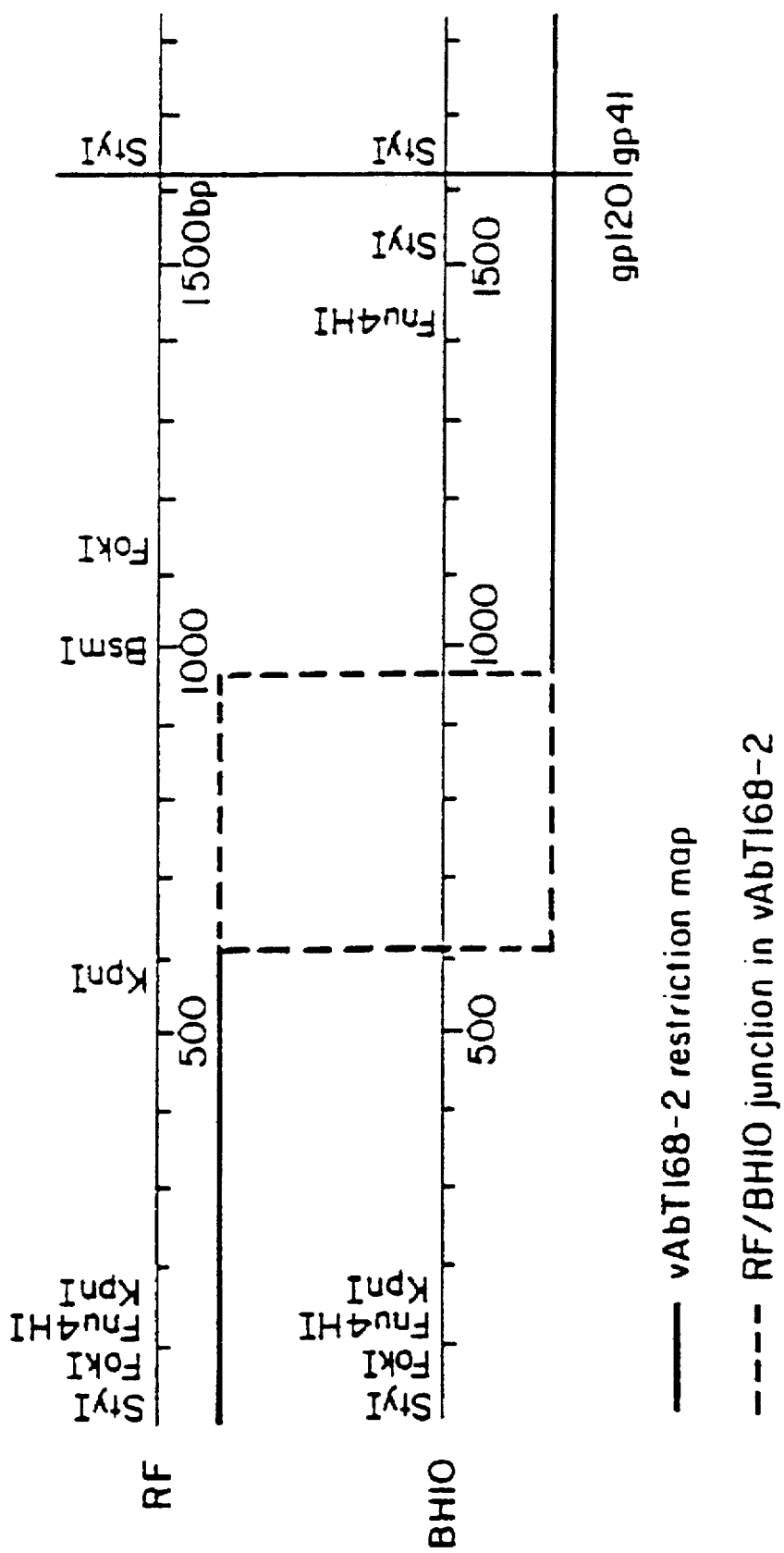
FIGS. 10A and 10B illustrate the restriction map (FIG. 10A) and nucleotide sequence (FIG. 10B) of another condensed env gene from the recombinant virus vAbT168-2.
Figure 10B:
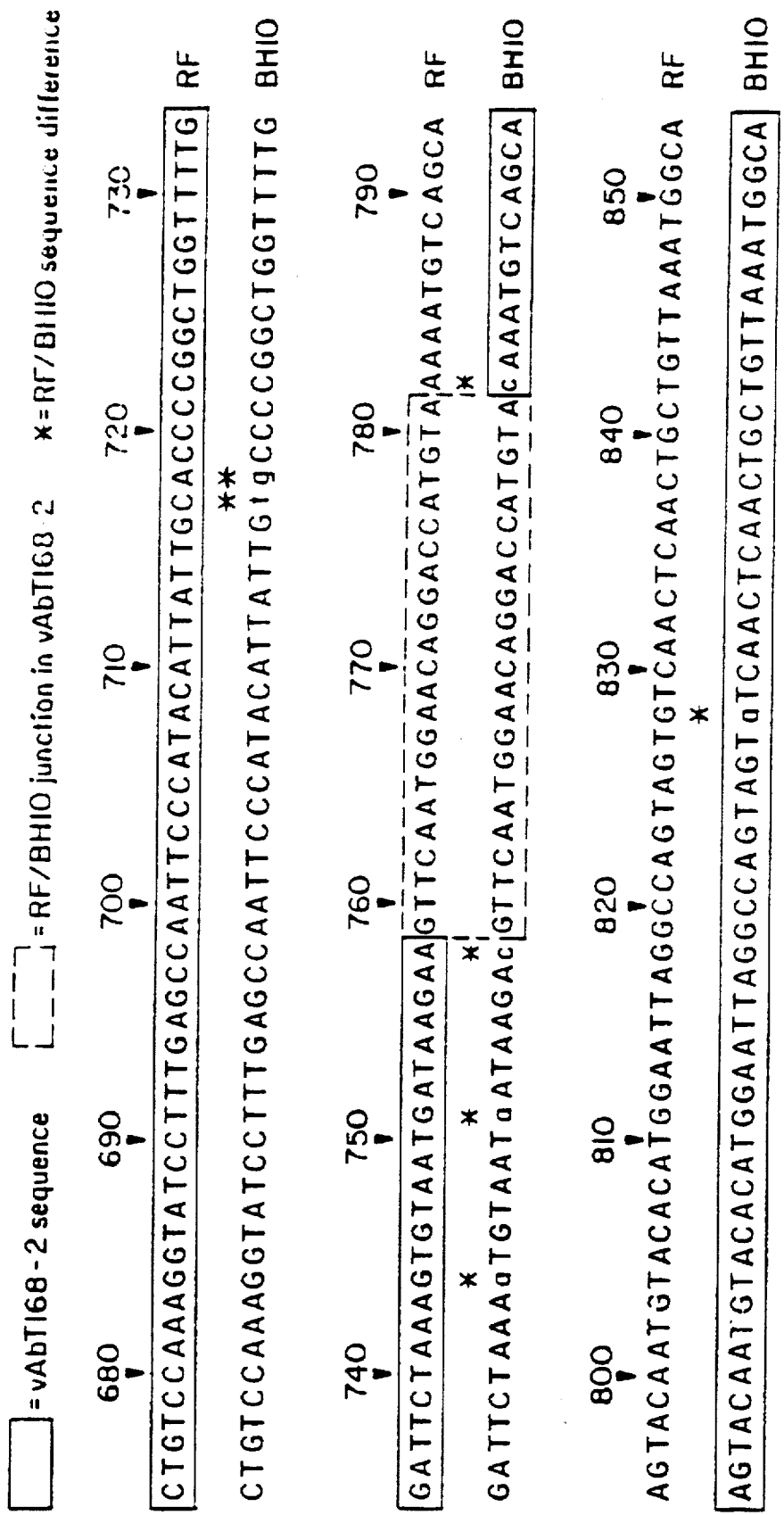

Vaccinia virus genomic DNA was also prepared from recombinant vAbT168-2 and was analyzed by Southern hybridization using HIV env DNA as a probe. The restriction map of the hybrid env gene from vAbT168-2 is shown in FIG. 10A. The map indicates that the RF/BH10 junction in vAbT168-2 is within a 360bp sequence between a KpnI and a BsmI site in the central region of gp120, between hypervariable regions $V_2$ and $V_3$. This region of vAbT168-2 was sequenced and is shown in FIG. 10B. In vAbT168-2, the RF/BH10 condensation event occurred within a conserved 23 bp sequence located between nucleotides 758 and 782. vAbT168-1 and vAbT168-2 are thus two recombinants containing different hybrid env-lacZ genes derived by vaccinia virus-mediated recombination between adjacent RF and BH10 env genes.

Figure 11:
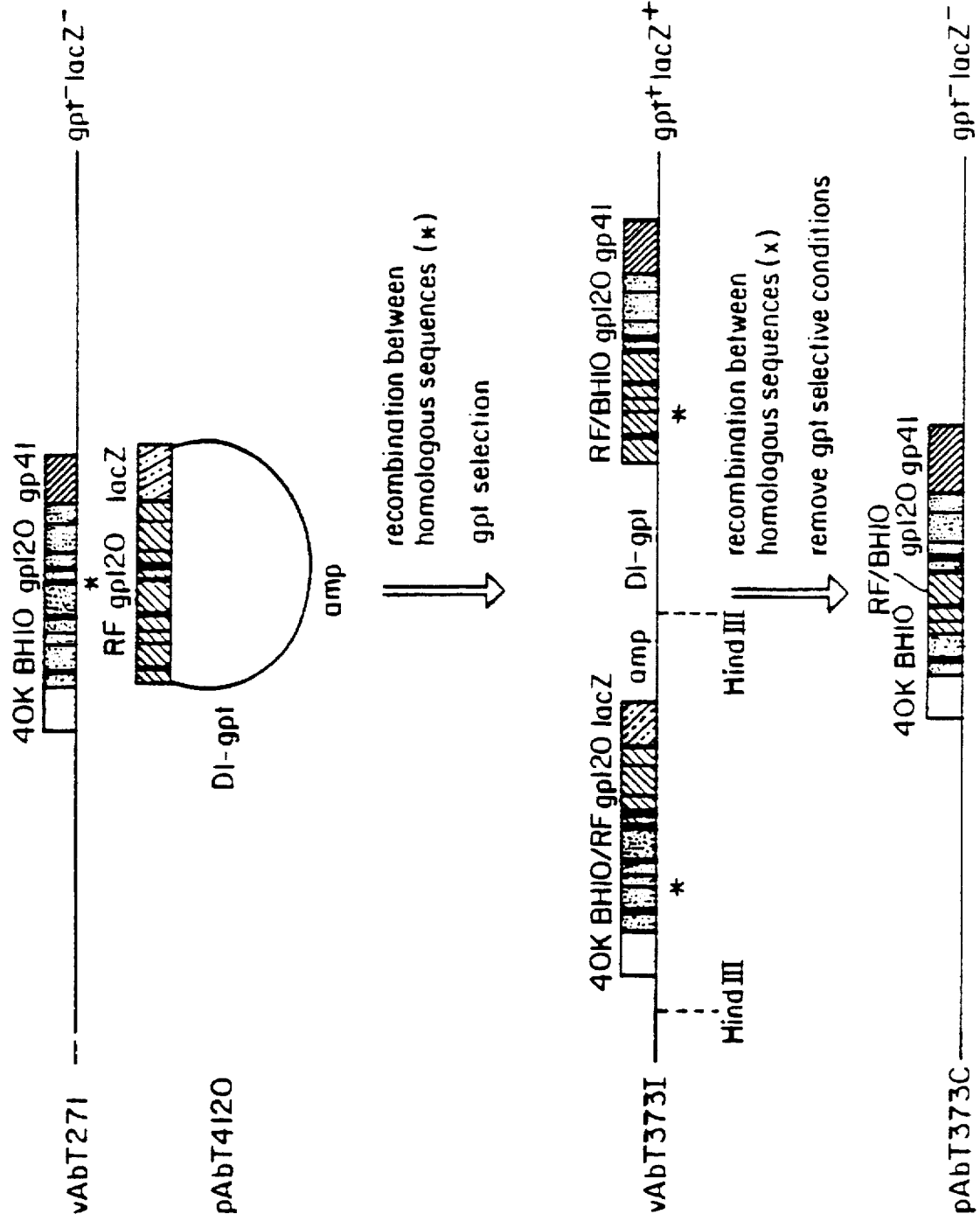
FIG. 11 shows the approach for generation of chimeric HIV env genes in vaccinia virus.
Figure 12:
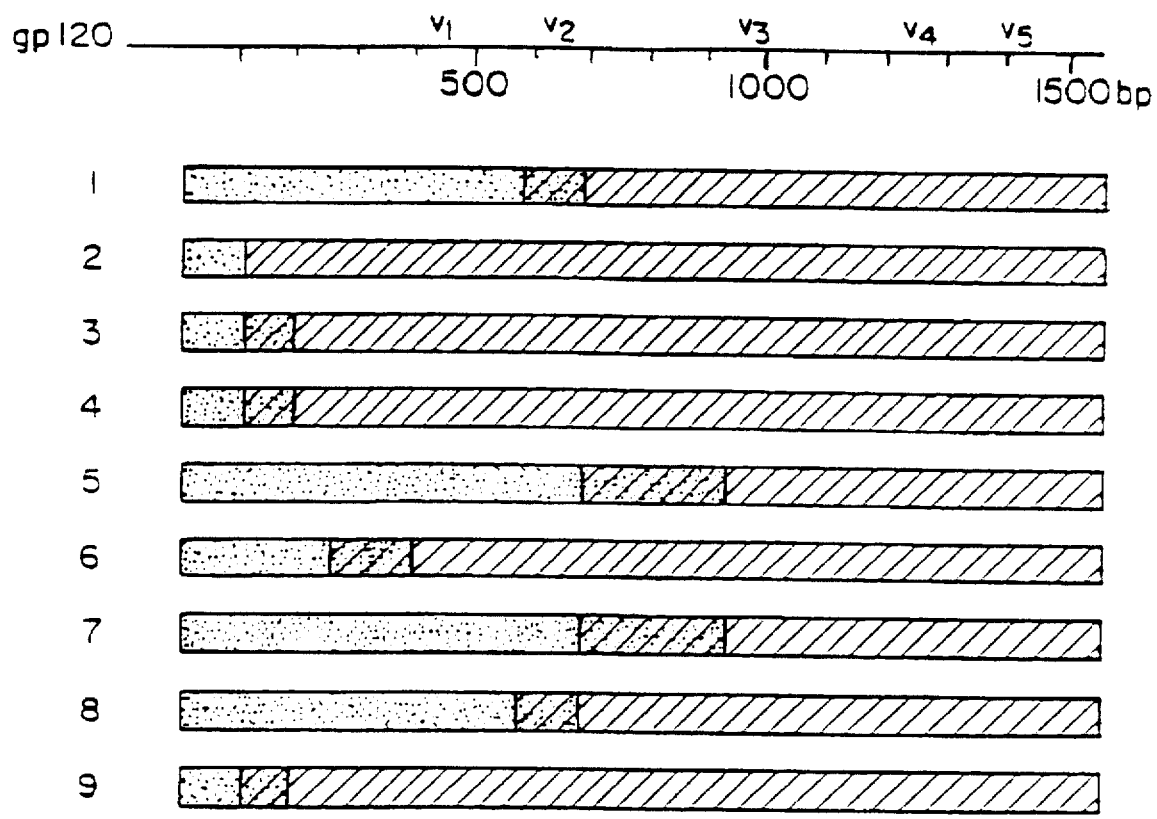
FIG. 12 shows the structure of hybrid env genes in intermediate recombinants.
Figure 13:
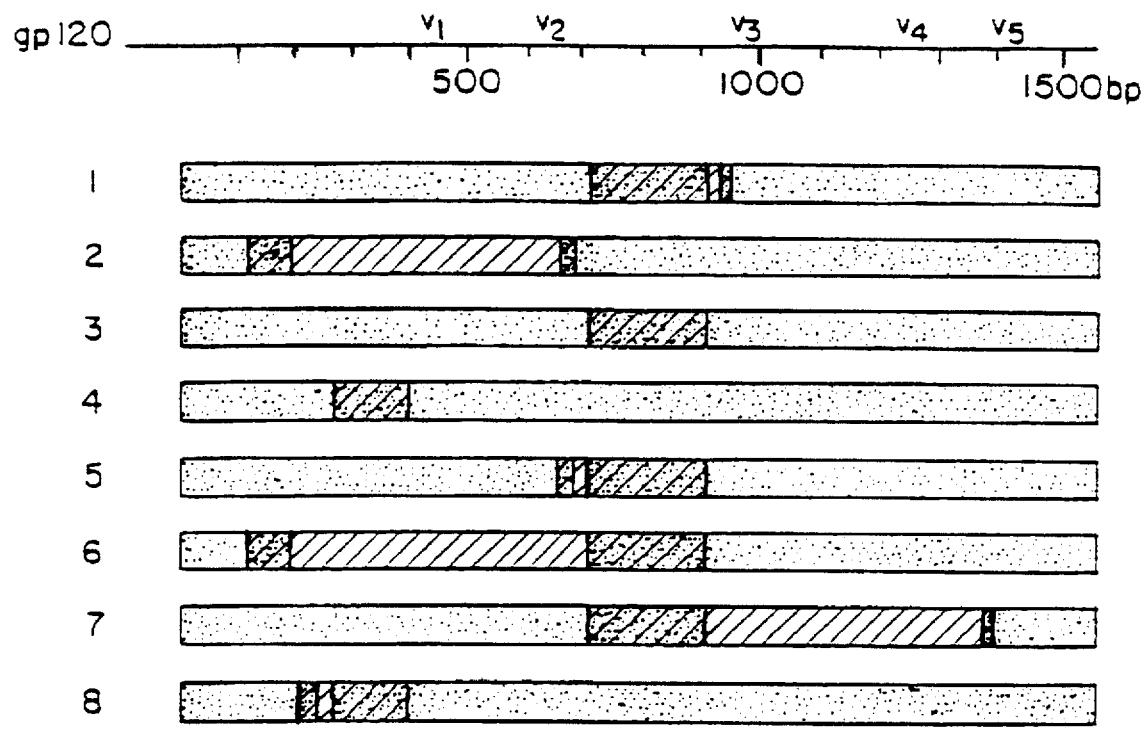
FIG. 13 shows the structure of hybrid env genes in condensed recombinants.

EXAMPLE 6
Generation of hybrid env genes (FIGS. 11, 12, 13)

Having demonstrated the feasibility of using vaccinia virus-mediated recombination to derive hybrid env-lacZ genes, the generation of populations of recombinant vaccinia containing full-length, chimeric env genes was undertaken. Approach 2 (FIG. 11) was used in this set of experiments. First, the HIV-1 BH10 env gene (including 11 nucleotides of 5' proximal and 105 nucleotides of 3' proximal untranslated sequences) was inserted, under the control of the vaccinia 40K promoter (designated H6 in Rosel et al., 1986 *J. Virol.* 60:436–449), into the HindIII M region of the vaccinia genome using host-range selection (See Smith, International patent application PCT/US89/02486, filed Jun. 7, 1989; this recombinant virus was designated vAbT271. Next, a plasmid vector, designated pAbT120, was constructed containing the 5' portion of the HIV-1 RF env gene fused at nucleotide 1449 (immediately following hypervariable region $V_5$ in gp120) to the lacZ gene. This vector also contained the gpt gene (Falkner and Moss, 1988, *J. Virol.* 62:1849–1854), under the control of the vaccinia D1 promoter (Lee-Chen et al., 1988, Virology 163:64–79), for selection of recombinants, and a bacterial replicon and ampicillin resistance gene for growth and selection in *E. coli*. Cells were infected with vAbT271 and then were transfected with pAbT120. A single recombination event between homologous regions of the BH10 env gene in vAbT271 and the RF env gene in pAbT120 would result in the genomic structure shown in FIG. 11, containing two hybrid env genes. Nine different recombinants, designated vAbT373I, were isolated and purified (using gpt and lacZ selection) to characterize these hybrid genes. The presence of a bacterial replicon and amp$^r$ gene facilitated the subcloning of the vaccinia genomic region containing the 5'-proximal hybrid gene. Genomic DNA preparations were digested with HindIII, self-ligated and used to transform *E. coli* to ampicillin-resistance. Restriction mapping revealed a number of different hybrid junctions in these intermediate recombinants (FIG. 12). In four of these recombinants (recombinants 1, 3, 5 and 6 as shown in FIG. 12), gpt-selective conditions were removed to allow the propagation of condensed virus containing a single, hybrid, full-length env gene. The lacZ gene served as a marker to distinguish condensed (colorless plaques) from uncondensed (blue plaques) virus. After four serial passages of virus under non-selective conditions, approximately 90% of the progeny plaques from each of the four populations were colorless, indicating that nearly all the viral genomes had condensed to a single env gene. The two junction regions in each of the hybrid genes from eight individual recombinants (two from each population) designated vAbT373C were mapped by restriction mapping of genomic DNA amplified by the polymerase chain reaction. Restriction mapping (FIG. 13) showed that each of the eight vAbT373C viruses contain a unique, hybrid env gene; no two were identical chimeras.

EXAMPLE 7
Immune response generated by vaccinia virus expressing hybrid env genes (FIG. 14)

Recombinants 1, 3, 5 and 6 (FIG. 12) from vAbT373I were passaged under non-selective conditions as described in Example 6 to generated four populations of virus containing a spectrum of hybrid BH10/RF/BH10 env genes. The four populations were mixed in equal proportions for immunization of rabbits. New Zealand white rabbits were immunized intravenously with $5 \times 10^7$ pfu of the vAbT373 mixture. Sera were taken prior to immunization and at two-week intervals post-immunization. Antibodies against vaccinia virus were detected by ELISA and antibodies against HIV envelope were detected by Western analysis. Neutralization assays were performed against HIV strains IIIB (similar to BH10) and RF. Results are shown in Table__. Antibodies raised against bAbT271 (BH10env) or vAbT272 (RFenv) neutralized HIV in a strain-specific manner, whereas antibodies raised against vAbT373 (mixed populations containing hybrid BH10/RF/BH10 env) neutralized both HIV strains IIIB and RF.

TABLE 1

IMMUNE RESPONSE AGAINST CHIMERIC HIV ENVELOPE GLYCOPROTEINS

| Immunogen | Antibodies | | Neutralization | |
|---|---|---|---|---|
| | α vaccinia | α HIV env | IIIB | RF |
| none | − | − | − | − |
| vAbT271 (BH10env) | + | + | + | − |
| vAbT272 (RFenv) | + | + | (−) | + |
| vAbT373 (population of hybrid BH10/RF/BH10 env) | + | + | + | + |

Deposit

The plasmid pABT4085 was placed on deposit at the American Type Culture Collection in Rockville, Md. on Oct. 6, 1988 and assigned Accession No. 67818.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of generating a family of hybrid genes, comprising the steps of:

(a) introducing a virus into a eukaryotic host cell, wherein the virus comprises at least two tandemly arranged DNA sequences, wherein at least one of the tandemly arranged DNA sequences is not in its native position with respect to the other sequence, wherein the tandemly arranged DNA sequences contain encoding regions and wherein the sequences are non-identical but share a region of sequence identity in an encoding region of the sequence of at least 10 nucleotides, and wherein a gene encoding a selectable marker is interposed between the tandemly arranged sequences; and (b) allowing the virus to replicate in the eukaryotic host cell under conditions which permit intramolecular recombination between the regions of sequence identity in the two tandemly arranged DNA sequences to produce the family of hybrid genes.

2. The method of claim 1, wherein the virus is a pox virus.

3. The method of claim 1, wherein each the DNA sequences encodes a protein.

4. The method of claim 1, wherein the selectable marker is selected from the group consisting of a thymidine kinase gene, E. coli Neo, E. Coli gpt gene, and vaccinia 29K gene.

5. A family of hybrid genes produced by the method of claim 1, wherein at least one hybrid gene is a single hybrid gene having the structure: tandem DNA sequence 1-tandem DNA sequence 2-tandem DNA sequence 1.

6. The method of claim 1 wherein the two tandemly arranged DNA sequences are at least about 30% homologous.

7. The method of claim 1 wherein the two tandemly arranged DNA sequences are at least about 80% homologous.

8. The method of claim 1 wherein the two tandemly arranged DNA sequences are at least about 90% homologous.

9. A family of hybrid genes produced by recombinant techniques from at least two tandemly arranged DNA sequences, wherein the tandemly arranged DNA sequences contain encoding regions, and wherein the sequences are non-identical but share a region of sequence identity in an encoding region of the sequences of at least 10 nucleotides, wherein at least one hybrid gene in the family of hybrid genes has the structure: tandem DNA sequence 1-tandem DNA sequence 2-tandem DNA sequence 1, a selectable marker is interposed between the tandemly arranged sequences.

* * * * *